US006632291B2

(12) United States Patent
Rabon et al.

(10) Patent No.: US 6,632,291 B2
(45) Date of Patent: Oct. 14, 2003

(54) METHODS AND COMPOSITIONS FOR CLEANING, RINSING, AND ANTIMICROBIAL TREATMENT OF MEDICAL EQUIPMENT

(75) Inventors: Reid Rabon, South St. Paul, MN (US); Sally K. Swart, Inver Grove Heights, MN (US); Denise Chandler, St. Paul, MN (US); Terrence P. Everson, Eagan, MN (US)

(73) Assignee: Ecolab Inc., St. Paul, MN (US)

( * ) Notice: Subject to any disclaimer, the term of this patent is extended or adjusted under 35 U.S.C. 154(b) by 13 days.

(21) Appl. No.: 09/816,695

(22) Filed: Mar. 23, 2001

(65) Prior Publication Data

US 2002/0173437 A1 Nov. 21, 2002

(51) Int. Cl.[7] .................................................. B08B 3/00
(52) U.S. Cl. .............................. 134/26; 134/2; 134/3; 134/25.1; 134/25.4; 134/27; 134/28; 134/29; 134/40; 134/41; 134/42; 510/108; 510/224; 510/233; 510/291; 510/513
(58) Field of Search ...................... 134/2, 3, 25.1, 134/25.4, 26, 27, 28, 29, 40, 41, 42; 510/108, 224, 233, 291, 513

(56) References Cited

U.S. PATENT DOCUMENTS

| 1,580,576 A | 4/1926 | Weidner |
| 1,949,264 A | 2/1934 | Bagley |
| 2,412,819 A | 12/1946 | MacMahon |
| 2,920,417 A | 1/1960 | Wertheimer |
| 2,927,900 A | 3/1960 | Shiraeff |
| 2,987,483 A | 6/1961 | Brooker |
| 3,048,548 A | 8/1962 | Martin et al. |
| 3,306,858 A | 2/1967 | Oberle |
| 3,334,147 A | 8/1967 | Brunelle et al. |
| 3,351,558 A | 11/1967 | Zimmerer |
| 3,382,178 A | 5/1968 | Lissant et al. |
| 3,390,092 A | 6/1968 | Keast et al. |
| 3,390,093 A | 6/1968 | Feierstein et al. |
| 3,392,121 A | 7/1968 | Gedge, III |
| 3,441,511 A | 4/1969 | Otrhalek et al. |
| 3,442,242 A | 5/1969 | Laskey et al. |
| 3,491,028 A | 1/1970 | Crotty et al. |
| 3,557,003 A | 1/1971 | Morris et al. |
| 3,639,286 A | 2/1972 | Ballestra et al. |
| 3,695,989 A | 10/1972 | Albert |
| 3,790,482 A | 2/1974 | Jones et al. |
| 3,816,320 A | 6/1974 | Corliss |
| 3,846,346 A | 11/1974 | Conn |
| 3,856,932 A | 12/1974 | May |
| 3,887,614 A | 6/1975 | Susuki et al. |
| 3,899,436 A | 8/1975 | Copeland et al. |
| 3,933,670 A | 1/1976 | Brill et al. |
| 3,936,386 A | 2/1976 | Corliss et al. |
| 3,941,710 A | 3/1976 | Gilbert et al. |
| 3,961,754 A | 6/1976 | Kuhns et al. |
| 3,985,669 A | 10/1976 | Krummel et al. |
| 4,000,080 A | 12/1976 | Bartolotia et al. |
| 4,072,621 A | 2/1978 | Rose |
| 4,083,795 A | 4/1978 | Joubert |
| 4,105,573 A | 8/1978 | Jacobsen |
| 4,147,650 A | 4/1979 | Sabatelli et al. |
| 4,148,603 A | 4/1979 | Schwuger et al. |
| 4,211,517 A | 7/1980 | Schmid |
| 4,212,761 A | 7/1980 | Ciaccio |
| 4,216,125 A | 8/1980 | Campbell et al. |
| 4,219,436 A | 8/1980 | Gromer et al. |
| 4,238,345 A | 12/1980 | Guilbert |

(List continued on next page.)

FOREIGN PATENT DOCUMENTS

| AU | 687075 | 2/1953 |
| EP | 0 161 596 A2 | 11/1985 |
| EP | 0 363 852 A1 | 4/1990 |
| EP | 0 364 840 A1 | 4/1990 |
| EP | 0 501 375 A1 | 9/1992 |
| EP | 0 364 840 B2 | 3/1996 |
| EP | 0 774 504 | 11/1996 |
| GB | 1 596 756 | 8/1981 |
| GB | 2 271 120 A | 4/1994 |
| JP | 61-87800 | 5/1986 |
| JP | 9-217100 | 8/1997 |
| WO | WO 92/02611 | 2/1992 |
| WO | WO 92/13061 | 8/1992 |
| WO | WO 93/21299 | 10/1993 |
| WO | WO 95/18215 | 7/1995 |
| WO | WO 96/06910 | 3/1996 |
| WO | WO 96/08555 | 3/1996 |
| WO | WO 96/41859 | 12/1996 |
| WO | WO 97/02753 | 1/1997 |
| WO | WO 97/05226 | 2/1997 |
| WO | WO 97/07190 | 2/1997 |
| WO | WO 98/25468 | 6/1998 |

OTHER PUBLICATIONS

Translation of German Published, Non–Examined Patent Application DE OS 28 10 999, filed under No. 28 10 999.1 on Mar. 14, 1978, and published on Sep. 21, 1978, claiming the priority of British Patent Application 1147–07; Title: Dishwasher Detergent: Applicant: Unilever N.V.; Representative: Dr. F. Lederer; Inventor: Wolfgang Prox.

*Primary Examiner*—Randy Gulakowski
*Assistant Examiner*—M. Kornakov
(74) *Attorney, Agent, or Firm*—Merchant & Gould P.C.

(57) ABSTRACT

The present invention relates to methods for cleaning, rinsing, and/or antimicrobial treatment of medical carts, medical cages, and other medical instruments, devices or equipment. The method for cleaning employs a solid alkaline, for example a solid carbonate, cleaning composition for cleaning the medical cart, cage, instrument, device, or equipment. The method for rinsing employs a solid neutral or neutralizing rinse composition for rinsing the medical cart, cage, instrument, device, or equipment. The method for antimicrobial treatment employs a solid, for example a solid quaternary ammonium or solid halogen, antimicrobial composition, for antimicrobial treatment of the medical cart, cage, instrument, device, or equipment.

78 Claims, No Drawings

U.S. PATENT DOCUMENTS

| | | |
|---|---|---|
| 4,243,543 A | 1/1981 | Guilbert et al. |
| 4,261,868 A | 4/1981 | Hora et al. |
| 4,268,406 A | 5/1981 | O'Brien et al. |
| 4,274,975 A | 6/1981 | Corkill et al. |
| 4,276,205 A | 6/1981 | Ferry |
| 4,284,532 A | 8/1981 | Leikhim et al. |
| 4,289,815 A | 9/1981 | Lee |
| 4,329,246 A | 5/1982 | Gilbert et al. |
| 4,348,293 A | 9/1982 | Clarke et al. |
| 4,359,413 A | 11/1982 | Ward et al. |
| 4,416,793 A | 11/1983 | Barrat et al. |
| 4,426,362 A | 1/1984 | Copeland et al. |
| 4,474,976 A | 10/1984 | Faltynek |
| 4,481,167 A | 11/1984 | Ginter et al. |
| 4,537,706 A | 8/1985 | Severson, Jr. |
| 4,587,031 A | 5/1986 | Kruse et al. |
| 4,594,175 A | 6/1986 | Copeland |
| 4,595,520 A | 6/1986 | Heile et al. |
| 4,605,509 A | 8/1986 | Corkill et al. |
| 4,608,187 A | 8/1986 | Chang |
| 4,608,189 A | 8/1986 | Koch et al. |
| 4,618,914 A | 10/1986 | Sato et al. |
| 4,624,713 A | 11/1986 | Morganson et al. |
| 4,664,848 A | 5/1987 | Oh et al. |
| 4,677,130 A | 6/1987 | Puzig |
| 4,680,134 A | 7/1987 | Heile et al. |
| 4,687,121 A | 8/1987 | Copeland |
| 4,690,305 A | 9/1987 | Copeland |
| 4,692,494 A | 9/1987 | Sonenstein |
| 4,695,284 A | 9/1987 | Hight |
| 4,698,181 A | 10/1987 | Lewis |
| 4,715,979 A | 12/1987 | Moore et al. |
| 4,725,376 A | 2/1988 | Copeland |
| 4,753,755 A | 6/1988 | Gansser |
| RE32,763 E | 10/1988 | Fernholtz et al. |
| RE32,818 E | 1/1989 | Fernholtz et al. |
| 4,826,661 A | 5/1989 | Copeland et al. |
| 4,830,773 A | 5/1989 | Olson |
| 4,836,951 A | 6/1989 | Totten et al. |
| 4,845,965 A | 7/1989 | Copeland et al. |
| 4,846,993 A | 7/1989 | Lentsch et al. |
| 4,858,449 A | 8/1989 | Lehn |
| 4,895,667 A | 1/1990 | Fox et al. |
| 4,965,012 A | 10/1990 | Olson |
| 4,983,315 A | 1/1991 | Glogowski et al. |
| 5,019,292 A | 5/1991 | Baeck et al. |
| 5,034,147 A | 7/1991 | Ramachandran |
| 5,061,392 A | 10/1991 | Bruegge et al. |
| 5,064,561 A | 11/1991 | Rouillard |
| 5,078,301 A | 1/1992 | Gladfelter et al. |
| 5,080,819 A | 1/1992 | Morganson et al. |
| 5,118,426 A | 6/1992 | Duncan et al. |
| 5,122,538 A | 6/1992 | Lokkesmoe et al. |
| 5,173,207 A | 12/1992 | Drapier et al. |
| 5,223,179 A | 6/1993 | Connor et al. |
| 5,234,719 A | 8/1993 | Richter et al. |
| 5,254,287 A | 10/1993 | Deleeuw et al. |
| 5,290,496 A | 3/1994 | Carduck et al. |
| 5,292,525 A | 3/1994 | Brenden et al. |
| 5,312,561 A | 5/1994 | Hoshino et al. |
| 5,316,688 A | 5/1994 | Gladfelter et al. |
| 5,358,653 A | 10/1994 | Gladfelter et al. |
| 5,382,377 A | 1/1995 | Raehse et al. |
| 5,407,700 A | 4/1995 | Man et al. |
| 5,419,850 A | 5/1995 | Backes et al. |
| 5,429,766 A | 7/1995 | Sone et al. |
| 5,447,648 A | 9/1995 | Steindorf |
| 5,451,336 A | 9/1995 | Schwadtke et al. |
| 5,474,698 A | 12/1995 | Rolando et al. |
| 5,494,817 A | 2/1996 | Chen |
| 5,516,449 A | 5/1996 | Agar et al. |
| 5,559,089 A | 9/1996 | Hartman et al. |
| 5,578,134 A | 11/1996 | Lentsch et al. |
| 5,589,099 A | 12/1996 | Baum |
| 5,650,017 A | 7/1997 | Gordon et al. |
| 5,665,694 A | 9/1997 | Backes et al. |
| 5,691,292 A | 11/1997 | Marshall et al. |
| 5,698,513 A * | 12/1997 | Schulz et al. ............... 510/192 |
| 5,763,378 A | 6/1998 | Painter et al. |
| 5,858,117 A | 1/1999 | Oakes et al. |
| 5,858,299 A | 1/1999 | Fernholz et al. |
| 5,861,366 A | 1/1999 | Ihns et al. |
| 5,876,514 A | 3/1999 | Rolando et al. |
| 5,990,068 A | 11/1999 | Brouwer et al. |
| 6,008,174 A | 12/1999 | Brouwer et al. |
| 6,017,864 A | 1/2000 | Brittain et al. |
| 6,017,869 A * | 1/2000 | Lu et al. ..................... 510/384 |
| 6,028,113 A * | 2/2000 | Scepanski .................... 422/28 |
| 6,060,444 A | 5/2000 | Schulz et al. |
| 6,136,769 A | 10/2000 | Asano et al. |
| 6,156,715 A | 12/2000 | Lentsch et al. |

* cited by examiner

METHODS AND COMPOSITIONS FOR CLEANING, RINSING, AND ANTIMICROBIAL TREATMENT OF MEDICAL EQUIPMENT

FIELD OF THE INVENTION

The present invention relates to methods for cleaning, rinsing, and/or antimicrobial treatment of medical carts, medical cages, and other medical instruments, devices or equipment. The method for cleaning employs a solid alkaline, for example a solid carbonate, cleaning composition for cleaning the medical cart, cage, instrument, device, or equipment. The method for rinsing employs a solid neutral or neutralizing rinse composition for rinsing the medical cart, cage, instrument, device, or equipment. The method for antimicrobial treatment employs a solid, for example a solid quaternary ammonium or solid halogen, antimicrobial composition, for antimicrobial treatment of the medical cart, cage, instrument, device, or equipment.

BACKGROUND OF THE INVENTION

Solid cleaning, rinsing, and antimicrobial compositions have not been employed in a medical environment, such as for cleaning, rinsing, or antimicrobial treatment of medical carts, medical cages, medical instruments, medical devices, or other medical equipment. The markets for equipment and supplies for washing medical carts, medical cages, medical devices or instruments, or other medical equipment are distinct from markets for cleaning other wares, such as kitchen wares. Surprisingly, equipment for washing medical carts is a different market from equipment for washing medical cages, which is in turn a different market than equipment for washing medical instruments or devices, and so on. As a result of this market segmentation, suppliers of equipment for washing medical carts, do not necessarily make equipment for washing medical cages (and vice versa), suppliers of equipment for washing medical cages do not necessarily make equipment for washing medical instruments or devices (and vice versa), and so on.

There remains a need to develop solid cleaning, rinse, and antimicrobial products and methods that can be employed in a medical or healthcare environment.

SUMMARY OF THE INVENTION

The present invention relates to methods for cleaning, rinsing, and/or antimicrobial treatment of medical carts, medical cages, and other medical instruments, devices or equipment. The method for cleaning employs a solid alkaline, for example a solid carbonate, cleaning composition for cleaning the medical cart, cage, instrument, device, or equipment. The method for rinsing employs a solid, for example solid neutral or neutralizing, rinse composition for rinsing the medical cart, cage, instrument, device, or equipment. The method for antimicrobial treatment employs a solid, for example a solid quaternary ammonium or solid halogen, antimicrobial composition, for antimicrobial treatment of the medical cart, cage, instrument, device, or equipment.

In a preferred embodiment, the method for cleaning a medical cart, cage, instrument, or device includes contacting the medical cart, cage, instrument, or device with the dissolved carbonate cleaning composition at a temperature at or above ambient temperature. Preferably, forming the dissolved carbonate cleaning composition includes dissolving a solid carbonate cleaning composition in water. Preferably, the solid carbonate cleaning composition includes about 10 to 80 wt-% of $Na_2CO_3$ and an effective sequestering amount of an organic phosphonate hardness sequestering agent. In this embodiment, the solid cleaning composition includes non-hydrated sodium carbonate and a binding agent comprising hydrated sodium carbonate and organic phosphonate.

In another embodiment, the solid carbonate cleaning composition also includes a metal protecting silicate. Preferred metal protecting silicates include an oxidized metal, $M_2O$, and $SiO_2$ in a ratio of about 1:1 to 1:5. Preferred metal protecting silicates are hydrated, and can include water content of about 5 to 25 wt-%. Preferred solid cleaning compositions include $Na_2O$ and $SiO_2$ in a ratio of about of about 1:1.5 to 1:2.5. In this embodiment, the solid cleaning composition preferably includes comprises about 10 to 30 wt. of alkali metal silicate.

In yet another embodiment, the binding agent is dispersed throughout the solid cleaning composition; includes the alkali metal carbonate hydrate and the organic sequestrant that form a binding agent comprising an organo phosphonate or an organo amino acetate and water; includes for each mole of the organic sequestrant, about 3 to 10 moles of the carbonate monohydrate and 5 to 15 moles of water; and has a melting transition temperature of greater than about 120° C. The binder preferably includes as an organic sequestrant amino tri(methylene phosphonic) acid or sodium salt thereof; 1-hydroxyethylidene-1,1-diphosphonic acid or sodium salt thereof, diethylenetriaminopenta(methylene phosphonic) acid or sodium salt thereof; β-alanine-N,N-diacetic acid or sodium salt thereof; diethylenetriaminepentaacetic acid or sodium salt thereof. In a preferred embodiment, the binder also includes a builder comprising sodium tripolyphosphate, sodium nitrilotriacetate, or mixtures thereof.

In another embodiment, the method of the invention includes rinsing a medical cart, cage, instrument, or device. Rinsing can include dissolving a solid rinse composition in water, and rinsing the medical cart, cage, instrument, or device with the dissolved rinse composition at a temperature at or above ambient temperature. Preferred solid rinse compositions include solid neutral rinse compositions and solid neutralizing rinse compositions. A preferred solid neutral rinse composition includes a nonionic surfactant and urea. A preferred solid neutralizing rinse composition includes a nonionic block surfactant with a cloud point greater than the rinse temperature employed in the method, a defoamer composition, and a water soluble casting agent.

In yet another embodiment, the method of the invention includes antimicrobial treatment of a medical cart, cage, instrument, or device. Antimicrobial treatment can include dissolving a solid antimicrobial composition in water, and contacting the medical cart, cage, instrument, or device with the dissolved antimicrobial composition at a temperature at or above ambient temperature. Preferred solid antimicrobial compositions include solid quaternary ammonium or solid halogen antimicrobial compositions. Preferred quaternary ammonium salts include octyl decyl dimethyl ammonium chloride, dioctyl dimethyl ammonium chloride, didecyl dimethyl ammonium chloride, dimethyl benzyl ammonium chloride, or a combination thereof, and the like. A preferred solid halogen antimicrobial agents includes a chlorinated phosphate, such as chlorinated trisodium phosphate. Contacting during antimicrobial treatment preferably continues for a time and at a concentration of antimicrobial composition sufficient for sanitizing the medical cart, cage, instrument, or device. In an embodiment, contacting during antimicrobial treatment preferably continues for a time and at a concentration of antimicrobial composition sufficient for disinfecting the medical cart, cage, instrument, or device.

The method of the invention can include one or more of cleaning, rinsing, and antimicrobial treatment of a medical cart, cage, instrument, device, or other medical equipment.

DETAILED DESCRIPTION OF THE INVENTION

Definitions

As used herein, the phrase "medical cart" refers to a cart employed in a health care environment to transport one or more medical instruments, devices, or equipment and that can benefit from cleaning with a use composition of a solid alkaline cleaning composition, rinsing with a use composition of a solid rinse composition, and/or antimicrobial treatment with a use composition of a solid antimicrobial composition. Medical carts include carts for transporting medical or dental devices or instruments or other medical or dental equipment in a health care environment, such as a hospital, clinic, dental or medical office, nursing home, extended care facility, or the like.

As used herein, the phrase "medical cage" refers to a cage employed in a health care environment to house and/or transport one or more animals employed in experiments, in clinical or toxicological testing, in diagnostics, or the like. Such animals include a rodent (e.g. a mouse or a rat), a rabbit, a dog, a cat, or the like. A medical cage typically includes an animal cage that actually houses the animal and which can be mounted on a wheeled rack. The medical cage can also include one or more containers or dispensers for animal food, one or more vessels or dispensers for water, and/or one or more systems for identifying the cart or animals. Medical cages can benefit from cleaning with a use composition of a solid alkaline cleaning composition, rinsing with a use composition of a solid rinse composition, and/or antimicrobial treatment with a use composition of a solid antimicrobial composition.

As used herein, the term "instrument" refers to the various medical or dental instruments or devices that can benefit from cleaning with a use composition of a solid alkaline cleaning composition, rinsing with a use composition of a solid rinse composition, and/or antimicrobial treatment with a use composition of a solid antimicrobial composition.

As used herein, the phrases "medical instrument", "dental instrument", "medical device", "dental device", "medical equipment", or "dental equipment" refer to instruments, devices, tools, appliances, apparatus, and equipment used in medicine or dentistry. Such instruments, devices, and equipment can be cold sterilized, soaked or washed and then heat sterilized, or otherwise benefit from cleaning, rinsing, or antimicrobial treatment according to the present invention. These various instruments, devices and equipment include, but are not limited to: diagnostic instruments, trays, pans, holders, racks, forceps, scissors, shears, saws (e.g. bone saws and their blades), hemostats, knives, chisels, rongeurs, files, nippers, drills, drill bits, rasps, burrs, spreaders, breakers, elevators, clamps, needle holders, carriers, clips, hooks, gouges, curettes, retractors, straightener, punches, extractors, scoops, keratomes, spatulas, expressors, trocars, dilators, cages, glassware, tubing, catheters, cannulas, plugs, stents, endoscopes (e.g., noninvasive flexible and rigid fiber optic endoscopes), endotracheal tubes, anesthesia breathing circuits, cytoscopes, arthoscopes and related equipment, and the like, or combinations thereof.

As used herein, solid composition refers to a composition in the form of a solid such as a powder, a flake, a granule, a pellet, a tablet, a lozenge, a puck, a briquette, a brick, a solid block, a unit dose, or another solid form known to those of skill in the art.

As used herein, dissolve can include partial or total dissolution. Partial dissolution can include suspension or precipitate in the dissolved composition.

As used herein, the term "sanitize" refers to use of physical or chemical processes to remove, inactivate, or destroy pathogenic organisms on an object or its surface and to render the object safe for handling, use of disposal.

As used herein, the term "disinfect" refers to destruction of pathogenic and other microorganisms by thermal or chemical processes destroying most pathogens, but not necessarily all microbial forms, such as bacterial spores.

As used herein, the term "microorganisms" refers to any noncellular or unicellular (including colonial) organism. Microorganisms include all prokaryotes. Microorganisms include bacteria (including cyanobacteria), lichens, microfungi, protozoa, virinos, viroids, viruses, and some algae. As used herein, the term "microbe" is synonymous with microorganism.

As used herein, ambient temperature refers to the temperature of the surroundings of the solid carbonate cleaning composition under normal conditions for storage or transportation. Although the product may be stored and transported at temperatures in the range of about 0° F. to about 100° F., ambient temperature preferably refers to room temperature of about 72° F. or 25° C.

As used herein, elevated temperature refers to temperatures above ambient temperature and commonly employed for washing, rinsing, antimicrobially treating or presoaking a medical cart, cage, instrument, or device. Washing can typically be conducted at elevated temperatures of about 30 to about 80° C., preferably about 35 to about 40° C., preferably about 60 to about 80° C. Rinsing can typically be conducted at elevated temperatures of about 40 to about 80° C. High temperature rinsing can typically be conducted at elevated temperatures of about 80 to about 95° C.

As used herein, bicarbonate, carbonate, carbonic acid salt, and the like are used to refer to a salt such as sodium carbonate, sodium bicarbonate, potassium carbonate, potassium bicarbonate or another salt obtained by or that can be visualized as being obtained by full or partial neutralization of carbonic acid. The weight percent of a salt of carbonate or bicarbonate can be expressed either as the weight percent of just the anionic carbonate or bicarbonate, or of the entire salt including the cation.

As used herein, basic or alkaline pH refers to pH greater than 7, preferably greater than 8 and up to about 14. Preferably basic or alkaline pH is in the range of about 8 to about 11.5. A preferred alkaline or basic pH value is in the range of about 10 to about 11.

As used herein, the term "cleaner" refers to a component added to a cleaning composition to provide cleaning power. Cleaners include surfactants, sources of alkalinity (e.g. alkali metal carbonates), chelators, antiredeposition agents, and the like, or combinations thereof.

As used herein, weight percent, percent by weight, % by weight, and the like are synonyms that refer to the concentration of a substance as the weight of that substance divided by the weight of the composition and multiplied by 100.

As used herein, the term "about" modifying the quantity of an ingredient in the compositions of the invention or employed in the methods of the invention refers at least to variation in the numerical quantity that can occur, for example, through typical measuring and liquid handling procedures used for making solids or use solutions in the real world; through inadvertent error in these procedures; through differences in the manufacture, source, or purity of the ingredients employed to make the compositions or carry out the methods; and the like. Whether or not modified by the term "about", the claims include equivalents to the quantities.

Methods and Compositions for Cleaning, Rinsing, and Antimicrobial Treatment of Medical Carts, Cages, Instruments, or Devices The present methods and compositions for cleaning a medical cart, cage, instrument, or device can be employed for cleaning a medical cart, cage, instrument, or device made of a variety of materials in a medical or health care environment. Typically, cleaning a medical cart, cage, instrument, or device includes contacting the medical cart, cage, instrument, or device with an aqueous cleaning composition formed by dissolving or suspending a solid alkaline, preferably a solid carbonate, cleaning composition. A method including cleaning can also involve rinsing the medical cart, cage, instrument, or device by rinsing or contacting with an aqueous rinse composition such as tap water, softened or treated water, or water including a rinse aid, preferably a neutral or neutralizing rinse composition. A method including cleaning can also involve antimicrobial treatment of the medical cart, cage, instrument, or device by contacting with an aqueous antimicrobial composition formed by dissolving or suspending a solid antimicrobial composition, preferably a solid quaternary ammonium or solid halogen antimicrobial composition.

Contacting with a cleaning composition can take place through manual application in a wash area or bay or through application by cart, cage, instrument, or device washing apparatus. In a manual method rinsing and/or antimicrobial treatment can also take place in the wash area or bay, or in a separate area or bay. A typical cart, cage, instrument, or device washing apparatus includes a wash station which applies the cleaning composition. Typically such a washing apparatus also includes a rinse station that can rinse the cart, cage, instrument, or device with water or another suitable rinse composition, such as a solid neutral or neutralizing rinse composition. Such a washing apparatus can also, optionally, include an antimicrobial treatment station that can contact the cart, cage, instrument, or device with a dissolved solid antimicrobial composition, such as a solid quaternary ammonium or solid halogen antimicrobial composition. A washing apparatus can conduct one or more of washing, rinsing, and/or antimicrobial treatment of steps at one, two, three, or more stations.

The cleaning composition employed either for manual or machine medical cart, cage, instrument, or device washing can be a solid alkaline cleaning composition, preferably a solid carbonate cleaning composition, which is described in greater detail herein below.

The solid carbonate cleaning compositions employed in the present invention can include a source of alkalinity preferably an alkali metal carbonate, an alkali metal salt of a sequestrant, preferably a potassium salt of an organophosphonate and, preferably, an E-form hydrate binding agent. Aspects of the present solid compositions, binding agents, and methods of making these compositions are described in U.S. patent application Ser. No. 08/989,824 filed Dec. 12, 1997, and entitled BINDING AGENT FOR SOLID BLOCK FUNCTIONAL MATERIAL; and U.S. Pat. No. 6,156,715 to Lentsch et al., issued Dec. 5, 2000, and entitled STABLE SOLID BLOCK METAL PROTECTING WAREWASHING DETERGENT COMPOSITION; the disclosures of which are incorporated herein by reference.

The present methods and compositions for rinsing a medical cart, cage, instrument, or device can be employed for rinsing a medical cart, cage, instrument, or device made of a variety of materials in a medical or health care environment. Typically, rinsing a medical cart, cage, instrument, or device includes rinsing the medical cart, cage, instrument, or device using an aqueous rinse composition formed by dissolving or suspending a solid rinse composition, preferably a solid neutral or neutralizing rinse composition. A method including rinsing can also involve cleaning a medical cart, cage, instrument, or device by contacting the medical cart, cage, instrument, or device with an aqueous cleaning composition formed by dissolving or suspending a solid alkaline, preferably a solid carbonate, cleaning composition. A method including rinsing can also involve antimicrobial treatment of the medical cart, cage, instrument, or device by contacting with an aqueous antimicrobial composition formed by dissolving or suspending a solid antimicrobial composition, preferably a solid quaternary ammonium or solid halogen antimicrobial composition.

Contacting with a rinsing composition can take place through manual application in a rinse area or bay or through application by cart, cage, instrument, or device washing and/or rinsing apparatus. In a manual method cleaning and/or antimicrobial treatment can also take place in the rinse area or bay, or in a separate area or bay. A typical cart, cage, instrument, or device washing apparatus includes a rinse station that can rinse the cart, cage, instrument, or device with a liquid rinse composition formed from a solid neutral or neutralizing rinse composition. Such a washing apparatus can also, optionally, include a washing and/or antimicrobial treatment station.

The rinse composition employed either for manual or machine medical cart, cage, instrument, or device rinsing can be a solid rinsing composition, preferably a solid neutral or neutralizing rinse composition, which is described in greater detail herein below.

The solid neutral rinse compositions employed in the present invention can include one or more nonionic surfactants, such as one or more EO PO copolymers, urea, and one or more silicones, such as one or more silicone dimethyl polysiloxane compounds. Aspects of the present solid neutral rinse compositions are described in U.S. Pat. No. 4,624,713, to Morganson, et al., issued Nov. 25, 1986, and entitled SOLID RINSE AIDS AND METHODS OF WAREWASHING UTILIZING SOLID RINSE AIDS; the disclosure of which is incorporated herein by reference.

The solid neutralizing rinse compositions employed in the present invention can include a nonionic block copolymer composition, defoamer composition, and a water soluble casting agent. Aspects of the present solid neutralizing rinse compositions are described in U.S. Pat. No. 5,589,099, to Baum, issued Dec. 31, 1996, and entitled LOW FOAMING RINSE AGENTS COMPRISING ETHYLENE OXIDE/ PROPYLENE OXIDE BLOCK COPOLYMER; the disclosure of which is incorporated herein by reference.

The present methods and compositions for antimicrobial treatment of a medical cart, cage, instrument, or device can be employed for antimicrobial treatment of a medical cart, cage, instrument, or device made of a variety of materials in a medical or health care environment. Typically, antimicrobial treatment of a medical cart, cage, instrument, or device includes contacting the medical cart, cage, instrument, or device with an aqueous antimicrobial composition formed by dissolving or suspending a solid antimicrobial composition, preferably a solid quaternary ammonium or solid halogen antimicrobial composition. The antimicrobial composition can be selected to provide preferential antibacterial activity.

Antimicrobial treatment can achieve varying degrees of antimicrobial effect, for example, up to and including sanitizing or disinfecting the medical cart, cage, instrument, or device. Sanitizing can be achieved with antimicrobial compositions including any of a variety of antimicrobial agents, such as quaternary ammonium antimicrobial agents, acid sanitizers, and other health care surface compatible antimicrobial agents. Sanitizing can be achieved by treatment times and with concentrations of antimicrobial compositions known to those of skill in the art. Such concentrations and times are typically longer than those required for only detectable reductions in populations of microorganisms. Disinfecting can be achieved with any of a variety of antimicrobial agents including quaternary ammonium antimicrobial agents. Disinfecting can employ antimicrobial agents more effective or potent than antimicrobial agents that result only in sanitizing. Disinfecting can be achieved by treatment times and with concentrations of antimicrobial compositions known to those of skill in the art. Such concentrations and times are typically longer than those required for sanitizing.

A method including antimicrobial treatment can also involve cleaning a medical cart, cage, instrument, or device by contacting the medical cart, cage, instrument, or device with an aqueous cleaning composition formed by dissolving or suspending a solid alkaline, preferably a solid carbonate, cleaning composition. A method including antimicrobial treatment can also involve rinsing the medical cart, cage, instrument, or device using an aqueous rinse composition formed by dissolving or suspending a solid rinse composition, preferably a solid neutral or neutralizing rinse composition.

Contacting with an antimicrobial composition can take place through manual application in an antimicrobial treatment area or bay or through application by cart, cage, instrument, or device washing and/or antimicrobial treatment apparatus. In a manual method cleaning and/or rinsing can also take place in the rinse area or bay, or in a separate area or bay. A cart, cage, instrument, or device washing apparatus can include an antimicrobial treatment station that sanitizes or disinfects the cart, cage, instrument, or device with a liquid antimicrobial composition formed from a solid quaternary ammonium or solid halogen antimicrobial composition. Such a washing apparatus can also, optionally, include a cleaning and/or rinsing station.

The antimicrobial composition employed either for manual or machine medical cart, cage, instrument, or device antimicrobial treatment can be a solid antimicrobial composition, preferably a solid quaternary ammonium or solid halogen antimicrobial composition, which is described in greater detail herein below.

Methods for Medical Cart Cleaning

Medical cart cleaning can be accomplished either manually or with a machine. Manual medical cart cleaning can include preparing a use composition of a solid carbonate cleaning composition and applying it to the medical cart. Applying typically includes wiping or scrubbing the medical cart with a brush, a towel, or a sponge soaked with the cleaning composition. Applying can also include spraying the cart with the use composition. Manual medical cart cleaning can also include preparing a use composition of a rinse composition, preferably a neutral rinse composition, and applying it to the medical cart. Applying a rinse composition can include spraying, pouring, or wiping the use composition onto the cart. Manual medical cart cleaning can also include preparing a use composition of a solid antimicrobial composition, preferably a solid quaternary ammonium or solid halogen antimicrobial composition, and applying it to the medical cart. Applying an antimicrobial composition can include spraying, pouring, or wiping the use composition onto the cart. Drying the medical cart, either manually or air drying, typically follows rinsing.

Machine cleaning of a medical cart can employ any of a variety of configurations of medical cart cleaning apparatus. Such apparatus can be adapted to dispense the solid carbonate cleaning composition employed in the methods of the invention. Such apparatus can also typically be adapted to dispense the solid, e.g., solid neutral or neutralizing, rinse composition employed in the methods of the invention. Such apparatus can also, optionally, be adapted to dispense the solid, e.g., solid quaternary ammonium or solid halogen, antimicrobial composition employed in the methods of the invention. A medical cart cleaning apparatus typically includes at least one chamber that houses the medical cart during washing, rinsing, and/or antimicrobial treatment.

Smaller medical cart cleaning apparatus typically include a single chamber sized to house, for example, 1–3 medical carts. Medical carts can be introduced into the smaller apparatus by an operator through a door or other coverable opening in the chamber. The apparatus then subjects the carts in the chamber to one or more of washing, rinsing, antimicrobial treatment, and/or drying cycles. Washing typically occurs by spraying the medical cart with a use wash composition. Rinsing typically occurs by spraying the medical cart with a use rinse composition. Optionally, antimicrobial treatment can occur by spraying the medical cart with a use antimicrobial composition. Drying can occur by blowing ambient or heated air, or by treating with steam. Medical carts can be removed from the chamber by an operator through the same door or other coverable opening or through an exit door or other coverable opening on an opposite side of the apparatus.

Larger medical cart cleaning apparatus typically includes a transport apparatus that transports one or several carts through one or more chambers including washing, rinsing, optionally antimicrobial treatment, and/or drying stations. Such a medical cart cleaning apparatus can resemble a touchless car wash sized and configured for cleaning medical carts instead of cars. Typically the cart is transported through the washing, rinsing, optional antimicrobial treatment, and/or drying stations by a track or rail apparatus while tipped at an acute angle from the horizontal, with its doors (if any) open. This tipping can keep the doors open and allow liquid to drain off any normally horizontal surfaces of the medical cart. The entry to a larger medical cart cleaning apparatus can be covered, for example, by a door or with hanging plastic strips that allow entry of carts but that retain use compositions in the apparatus. The wash station typically sprays the medical cart with use wash composition. A rinse station typically sprays the medical cart with use rinse composition. An optional antimicrobial treatment station typically sprays the medical cart with use antimicrobial composition. At the drying station, blowers blow ambient or heated air on the cart, or the cart is steam treated. Alternatively, the cart can be removed from the apparatus and towel dried. One or more stations can be at different, overlapping, or the same locations. The exit from the apparatus can be covered in the same manner as the entrance.

Mechanical cart washers can employ up to about 30 to about 40 gallons of use composition of cleaning composition per wash cycle, up to about 30 to about 40 gallons of use composition rinse composition per rinse cycle, and, optionally, up to about 30 to about 40 gallons of use antimicrobial composition per antimicrobial treatment cycle. The actual amount of cleaning, rinsing, or antimicrobial composition used will be based on the judgment of the user, and will depend upon factors such as the particular product formulation of the composition, the concentration of the composition, the number of soiled carts to be cleaned and the degree of soiling of the carts.

A machine that washes medical carts can also be employed to wash other wheeled medical equipment or supplies such as wheel chairs, wheeled stands, such as those that hold intravenous bags, tubes and pumps, wheeled (metro) shelves, and the like.

Methods for Medical Cage Cleaning

Medical cage cleaning can be accomplished either manually or with a machine. Manual medical cage cleaning can include preparing a use composition of a solid carbonate cleaning composition and applying it to the medical cage. Applying typically includes wiping or scrubbing the medical cage with a brush, a towel, or a sponge soaked with the cleaning composition. Applying can also include spraying the cage with the use composition. Manual medical cage cleaning can also include preparing a use composition of a solid rinse composition, preferably a solid neutral or neutralizing rinse composition, and applying it to the medical cage. Applying a rinse composition can include spraying, pouring, or wiping the use composition onto the cage. Manual medical cage cleaning can also include preparing a use composition of a solid antimicrobial composition, preferably a solid quaternary ammonium or solid halogen antimicrobial composition, and applying it to the medical cage. Applying an antimicrobial composition can include spraying, pouring, or wiping the use composition onto the cage. Drying the medical cage, either manually or air drying, typically follows rinsing.

Machine cleaning of a medical cage can employ any of a variety of configurations of medical cage cleaning apparatus. Such apparatus can be adapted to dispense the solid carbonate cleaning composition employed in the methods of the invention. Such apparatus can also typically be adapted to dispense the solid, e.g., solid neutral or neutralizing, rinse composition employed in the methods of the invention. Such apparatus can also, optionally, be adapted to dispense the solid, e.g., solid quaternary ammonium or solid halogen, antimicrobial composition employed in the methods of the invention. A medical cage cleaning apparatus typically includes at least one chamber that houses the medical cage during washing, rinsing, and/or antimicrobial treatment.

Smaller medical cage cleaning apparatus typically include a single chamber sized to house, for example, 1–3 medical cages. Medical cages can be introduced into the smaller apparatus by an operator through a door or other coverable opening in the chamber. The apparatus then subjects the cages in the chamber to one or more of washing, rinsing, antimicrobial treatment, and/or drying cycles. Washing typically occurs by spraying the medical cage with a use wash composition. Rinsing typically occurs by spraying the medical cage with a use rinse composition. Optionally, antimicrobial treatment can occur by spraying the medical cage with a use antimicrobial composition. Drying can occur by blowing ambient or heated air, or by treating with steam. Medical cages can be removed from the chamber by an operator through the same door or other coverable opening or through an exit door or other coverable opening on an opposite, or "clean", side of the apparatus.

Larger medical cage cleaning apparatus typically includes a transport apparatus that transports one or several cages through one or more chambers including washing, rinsing, optionally antimicrobial treatment, and/or drying stations. Such a medical cage cleaning apparatus can resemble a touchless car wash sized and configured for cleaning medical cages instead of cars. Typically the cage is transported through the washing, rinsing, optionally antimicrobial treatment, and/or drying stations by a track or rail apparatus. The entry to a larger medical cage cleaning apparatus can be covered, for example, by a door or with hanging plastic strips that allow entry of cages but that retain use compositions in the apparatus. The wash station typically sprays the medical cage with use wash composition. A rinse station typically sprays the medical cage with use rinse composition. An optional antimicrobial treatment station typically sprays the medical cage with use antimicrobial composition. At the drying station, blowers blow ambient or heated air on the cage, or the cage is steam treated. Alternatively, the cage can be removed from the apparatus and towel dried. One or more stations can be at different, overlapping, or the same locations. The exit from the apparatus can be covered in the same manner as the entrance.

Mechanical cage washers can employ up to about 30 to about 40 gallons of use cleaning composition per wash cycle, up to about 30 to about 40 gallons of use rinse composition per rinse cycle, and, optionally, up to about 30 to about 40 gallons of use antimicrobial composition per antimicrobial treatment cycle. The actual amount of cleaning, rinsing, and/or antimicrobial composition used will be based on the judgment of the user, and will depend upon factors such as the particular product formulation of the composition, the concentration of the composition, the number of soiled cages to be cleaned and the degree of soiling of the cages.

Methods for Instrument Cleaning

Instrument cleaning can be accomplished either manually or with a machine. Manual instrument cleaning can include preparing a use composition of a solid carbonate cleaning composition and applying it to the instrument. Applying typically includes wiping or scrubbing the instrument with a brush, a cloth, or a sponge soaked with the cleaning composition. Applying can also include spraying the instrument with the use composition. Manual instrument cleaning can also include preparing a use rinse composition, preferably a neutral or neutralizing rinse composition, and applying it to the instrument. Applying a rinse composition can include spraying, pouring, or wiping the use composition onto the instrument. Manual medical instrument cleaning can also include preparing a use composition of a solid antimicrobial composition, preferably a solid quaternary ammonium or solid halogen antimicrobial composition, and applying it to the medical instrument. Applying an antimicrobial composition can include spraying, pouring, or wiping the use composition onto the instrument. Drying the instrument, either manually or air drying, typically follows rinsing.

Machine cleaning of an instrument can employ any of a variety of configurations of instrument cleaning apparatus. Such apparatus can be adapted to dispense the solid carbonate cleaning composition employed in the methods of the invention. Such apparatus can also typically be adapted to dispense the solid, e.g., solid neutral or neutralizing, rinse composition employed in the methods of the invention. Such apparatus can also, optionally, be adapted to dispense the solid, e.g., solid quaternary ammonium or solid halogen, antimicrobial composition employed in the methods of the invention. An instrument cleaning apparatus typically transports a basket containing instruments through the chamber or chambers. The apparatus typically includes at least one chamber that houses the instrument during washing, rinsing, and/or antimicrobial treatment cycles.

Preferred apparatus carries out 2 to 4 different washing, rinsing, antimicrobial treatment, or other treating cycles. These cycles can include a pre-cleaning cycle including contacting, typically spraying, the instrument with an enzyme containing composition, such as an enzyme containing solid carbonate cleaning composition or a stabilized enzyme carbonate cleaning composition. If used, this pre-cleaning cycle precedes the washing cycle. The washing cycle includes contacting, typically spraying, the instrument with a solid carbonate cleaning composition. A rinsing cycle can follow the washing cycle. The rinsing cycle includes contacting, typically spraying, the instrument with a rinsing composition, preferably a neutral rinsing composition. These cycles can also include a lubricating cycle. The lubricating cycle includes contacting, typically spraying, the instrument with a lubricating composition, such as an oil based emulsion or "milk bath". Lubricating oil based emulsions or milk baths are known to those of skill in the art. The pre-cleaning and/or lubricating steps can be conducted manually, with the apparatus conducting at least the washing and rinsing cycles.

Mechanical instrument washers can employ up to about 3 to about 5 gallons of use composition of cleaning composition per wash cycle, up to about 3 to about 5 gallons of use composition rinse composition per rinse cycle, and up to about 3 to about 5 gallons of use composition antimicrobial composition per antimicrobial treatment cycle. The actual amount of cleaning or rinsing composition used will be based on the judgment of the user, and will depend upon factors such as the particular product formulation of the composition, the concentration of the composition, the number of soiled instruments to be cleaned and the degree of soiling of the instruments.

Solid Carbonate Cleaning Compositions

The present solid carbonate cleaning compositions are typically solids based on a matrix of carbonate and bicarbonate, but including additional ingredients The solid matrix includes conventional alkaline carbonate cleaning agent, a sequestering agent, and other active ingredients that will vary according to the type of composition being manufactured. Preferred ingredients are as follows:

Solid Matrix Composition

| Chemical | Percent Range |
| --- | --- |
| Alkali metal salt of an Organophosphonate | 1–30 wt-%; preferably 3–15 wt-% of a potassium salt thereof |
| Water | 5–15 wt-%; preferably 5–12 wt-% |
| Alkali Metal Carbonate | 25–80 wt-%; preferably 30–55 wt-% |
| Surfactant | 0 to 25 wt-%; preferably 0.1–20 wt-% |

Solidification of this material typically produces an E-form hydrate binder composition. This hydrate binder is not a simple hydrate of the carbonate component, as is described briefly below and in greater detail in U.S. patent application Ser. No. 08/989,824 and U.S. Pat. No. 6,156,715, which have been incorporated herein by reference.

Alkaline Source

The solid carbonate cleaning composition produced according to the invention can include effective amounts of one or more alkaline sources to enhance cleaning of a substrate and improve soil removal performance of the composition. The alkaline matrix can be bound into a solid due to the presence of the binder hydrate composition including its water of hydration. Such a composition includes about 10–80 wt-%, preferably about 15–70 wt-% of an alkali metal carbonate source, most preferably about 20–60 wt-%. A metal carbonate such as sodium or potassium carbonate, bicarbonate, sesquicarbonate, mixtures thereof and the like can be used. The total alkalinity source can include less than about 10 wt-%, preferably about 5 wt-% or less, of an alkali metal hydroxide. The alkali metal hydroxide is preferably present in an amount that does not disadvantageously alter the balance of carbonate to bicarbonate but that can, for example, balance other added acidic materials. Preferably carbonate and bicarbonate are the primary sources of alkalinity, with any other source present only to neutralize other acidic materials.

A highly effective detergent material can be made with little water (i.e. less than 11.5 wt-%, preferably less than 10 wt-% water) based on the total amount of solid. The carbonate based materials can be made in extrusion methods with little water. The total amount of water present in the solid block detergents of the invention is preferably less than about 11 to 12 wt-% water based on the total chemical composition (not including the weight of the container, if any). The preferred solid detergent includes less than about 2.0, more preferably about 0.9 to 1.7 moles of water per each mole of carbonate. Preferred stable solid detergents will include about 5 to 20 wt-%, preferably 10 to 15 wt-% anhydrous carbonate. The balance of the carbonate includes carbonate monohydrate. Further, some small amount of sodium carbonate monohydrate can be used in the manufacture of the detergent, however, such water of hydration is used in this calculation.

The alkali metal carbonate can be used in a formulation that includes an effective amount of a hardness sequestering agent that both sequesters hardness ions such as calcium, magnesium and manganese but also provides soil removal and suspension properties. The formulations can also contain a surfactant system that, in combination with the sodium carbonate and other components, effectively removes soils at typical use temperatures and concentrations. The solid detergent can also contain other common additives such as surfactants, builders, thickeners, soil anti-redeposition agents, defoamers, rinse aids, dyes, perfumes, etc.

Binder Composition

A preferred binding agent includes a solid matrix based on a combination of a carbonate hydrate and a non-hydrated carbonate species solidified by a hydrated species, referred to herein as the E-form hydrate or binder. Preferably, the E-form binder includes a carbonate salt, an organic phosphonate or acetate component and water. In the E-form hydrate binder, for each mole of organic phosphonate or amino acetate, there is about 3 to 10 molar parts of alkali metal carbonate monohydrate and 5 to 15 molar parts of water based on the binder weight. Typically, the E-form hydrate is dispersed throughout the solid. The solid can contain other cleaning ingredients and a controlled amount of water. The solid detergent can use a substantial proportion, sufficient to obtain non-corrosive cleaning properties, of a hydrated carbonate and a non-hydrated carbonate formed into solid.

The binder typically includes an alkali metal carbonate, an organic phosphonate sequestrant and water. A solid detergent can be manufactured including sodium carbonate, an organic phosphonate or acetate, less than about 1.3 moles of water per each mole of sodium carbonate and other optional ingredients including nonionic surfactants, defoamers, enzymes and the like. Under these conditions, a solid functional material can be manufactured from a mixture of ingredients having both hydrated sodium carbonate and non-hydrated sodium carbonate. The mixture can be formed into a solid using a hydration complex including a portion of the sodium carbonate, the organic phosphonate or acetate sequestrant and water. The majority of the water present forms carbonate monohydrate within the overall complex. The complex can be a substantially amorphous material substantially free of crystalline structure as shown in x-ray crystallographic studies. The material solidified by the complex can be in large part, about 10 to 85 wt. %, $Na_2CO_3.H_2O$ (monohydrate); less than about 25 wt. %, preferably about 0.1 to 15 wt. % anhydrous carbonate. Such solid detergent materials are preferably substantially free of a component that can compete with the alkali metal carbonate or the E-form material for water of hydration and interfere with solidification.

Additional Ingredients

The present solid carbonate cleaning composition can include any of a variety of ingredients typically included in solid carbonate or other cleaning compositions. Such ingredients include, but are not limited to, a surfactant, a metal protecting silicate, a chelating or sequestering agent, a builder, secondary hardening agent or solubility modifier, detergent filler, defoamer, anti-redeposition agent, a threshold agent or system, polyol, wetting agent, hydrotrope, as well as pigments or dye, fragrance, carbohydrate, and the like. Adjuvants and other additive ingredients will vary according to the type of composition being manufactured.

Such additional ingredients can be preformulated with the solid carbonate cleaning composition of the invention or added to the system simultaneously, or even after, the addition of the solid carbonate composition. The composition of the invention can also contain any number of other constituents as necessitated by the application, which are known to those of skill in the art and which can facilitate the activity of the present invention.

Chelating Agents or Sequestrants

Chelating agents or sequestrants generally useful in the present compositions include alkyl diamine polyacetic acid-type chelating agents such as EDTA (ethylene diamine tetraacetate tetrasodium salt), acrylic and polyacrylic acid-type stabilizing agents, phosphonic acid, and phosphonate-type chelating agents among others. Preferable sequestrants include phosphonic acids and phosphonate salts including 1-hydroxy ethylidene-1,1-diphosphonic acid ($CH_3C(PO_3H_2)_2OH$) (HEDP), amino[tri(methylene phosphonic acid)] (ATMP), ethylene diamine[tetra methylene-phosphonic acid)], 2-phosphene butane-1,2,4-tricarboxylic acid (PBTC), as well as the alkyl metal salts, ammonium salts, or alkyloyl amine salts, such as mono, di, or tetra-ethanolamine salts.

Amino phosphates and phosphonates are also suitable for use as chelating agents in the compositions of the invention and include ethylene diamine (tetramethylene phosphonates), nitrilotrismethylene phosphates, diethylenetriamine (pentamethylene phosphonates). These amino phosphonates commonly contain alkyl or alkaline groups with less than 8 carbon atoms. The phosphonic acid may also include a low molecular weight phosphonopolycarboxylic acid such as one having about 2–4 carboxylic acid moieties and about 1–3 phosphonic acid groups. Such acids include 1-phosphono-1-methylsuccinic acid, phosphonosuccinic acid and 2-phosphonobutane-1,2,4-tricarboxylic acid.

Commercially available chelating agents include phosphonates sold under the trade name DEQUEST® including, for example, 1-hydroxyethylidene-1,1-diphosphonic acid, available from Monsanto Industrial Chemicals Co., St. Louis, Mo., as DEQUEST® 2010; amino(tri (methylenephosphonic acid)), ($N[CH_2PO_3H_2]_3$), available from Monsanto as DEQUEST® 2000; ethylenediamine [tetra(methylenephosphonic acid)] available from Monsanto as DEQUEST® 2041; and 2-phosphonobutane-1,2,4-tricarboxylic acid available from Mobay Chemical Corporation, Inorganic Chemicals Division, Pittsburgh, Pa., as Bayhibit AM; and amino[tri(methylene phosphonic acid)] (ATMP) available as Briquest 301–50A: Amino Tri (Methylene Phosphonic Acid) (ATMP), 50%, low ammonia from Albright & Wilson.

The above-mentioned phosphonic acids can also be used in the form of water soluble acid salts, particularly the alkali metal salts, such as sodium or potassium; the ammonium salts or the alkylol amine salts where the alkylol has 2 to 3 carbon atoms, such as mono-, di-, or triethanolamine salts. If desired, mixtures of the individual phosphonic acids or their acid salts can also be used.

Preferred sequestrants for use in compositions with an E-form binder include an organic phosphonate or an amino acetate. Organic phosphonates that are useful in the E-Form hydrate of the invention include, for example 1-hydroxyethane-1,1-diphosphonic acid, aminotrimethylene phosphonic acid, diethylenetriaminepenta (methylenephosphonic acid) and other similar organic phosphonates. Amino carboxylic acids, such as amino acetates, that useful in the E-Form binder include, for example, N-hydroxyethylaminodiacetic acid, an hydroxyethylenediaminetetraacetic acid, diethylenetriaminepentaacetic acid, nitrilotriacetic acid (NTA), ethylenediaminetetraacetic acid (EDTA), N-hydroxyethyl-ethylenediaminetriacetic acid (HEDTA), diethylenetriaminepentaacetic acid (DTPA), and other similar acids having an amino group with a carboxylic acid substituent. Preferred cleaning compositions with an E-form binder include about 0.1–70 wt. %, preferably from about 5–60 wt. %, of a chelating/sequestering agent.

Builder

Detergent builders can optionally be included in the solid carbonate cleaning composition of the present invention for purposes including assisting in controlling mineral hardness. Inorganic as well as organic builders can be used. The level of builder can vary widely depending upon the end use of the composition and its desired physical form.

Inorganic or phosphate-containing detergent builders include alkali metal, ammonium and alkanolammonium salts of polyphosphates (e.g. tripolyphosphates, pyrophosphates, and glassy polymeric meta-phosphates). Non-phosphate builders may also be used. These can include phytic acid, silicates, alkali metal carbonates (e.g. carbonates, bicarbonates, and sesquicarbonates), sulphates, aluminosilicates, monomeric polycarboxylates, homo or copolymeric polycarboxylic acids or their salts in which the polycarboxylic acid includes at least two carboxylic radicals separated from each other by not more than two carbon atoms, citrates, succinates, and the like. Preferred builders include citrate builders, e.g., citric acid and soluble salts thereof, due to their ability to enhance detergency of a soap or detergent solution and their availability from renewable resources and their biodegradability.

Surfactant

The surfactant or surfactant admixture of the present invention can be selected from water soluble or water dispersible nonionic, semi-polar nonionic, anionic, cationic, amphoteric, zwitterionic surface-active agents, or any combination thereof Anionic and nonionic agents are preferred. The particular surfactant or surfactant mixture chosen for use in the process and products of this invention can depend on the conditions of final utility, including method of manufacture, physical product form, use pH, use temperature, foam control, and soil type. Preferably, the cleaning composition comprises a cleaning agent in an amount effective to provide a desired level of cleaning, preferably about 0–20 wt %, more preferably about 1.5–15 wt %. A typical listing of the classes and species of surfactants useful herein appears in U.S. Pat. No. 3,664,961 issued May 23, 1972, to Norris.

Nonionic surfactants useful in cleaning compositions, include those having a polyalkylene oxide polymer as a portion of the surfactant molecule. Such nonionic surfactants include, for example, chlorine-, benzyl-, methyl-, ethyl-, propyl-, butyl- and other like alkyl-capped polyethylene glycol ethers of fatty alcohols; polyalkylene oxide free nonionics such as alkyl polyglycosides; sorbitan and sucrose esters and their ethoxylates; alkoxylated ethylene diamine; alcohol alkoxylates such as alcohol ethoxylate propoxylates, alcohol propoxylates, alcohol propoxylate ethoxylate propoxylates, alcohol ethoxylate butoxylates, and the like; nonylphenol ethoxylate, polyoxyethylene glycol ethers and the like; carboxylic acid esters such as glycerol esters, polyoxyethylene esters, ethoxylated and glycol esters of fatty acids, and the like; carboxylic amides such as diethanolamine condensates, monoalkanolamine condensates, polyoxyethylene fatty acid amides, and the like; and polyalkylene oxide block copolymers including an ethylene oxide/propylene oxide block copolymer such as those commercially available under the trademark PLURONIC® (BASF-Wyandotte), and the like; and other like nonionic compounds. Silicone surfactants such as the ABIL® B8852 can also be used.

Preferred surfactants include nonionic surfactants, such as alkylphenol alkoxylates. Alkylphenol alkoxylates include condensation products of one mole of alkyl phenol wherein the alkyl chain, of straight chain or branched chain configuration, or of single or dual alkyl constituent, contains from about 8 to about 18 carbon atoms with from about 3 to about 50 moles of ethylene oxide. Preferred alkyl phenol alkoxylates include having a $C_{1-12}$ alkyl group and from about 3 to 16 moles of alkylene oxide, such as nonylphenol ethoxylates, such as nonylphenol ethoxylate 9.5.

Anionic surfactants useful in the present cleaning compositions, include, for example, carboxylates such as alkylcarboxylates (carboxylic acid salts) and polyalkoxycarboxylates, alcohol ethoxylate carboxylates, nonylphenol ethoxylate carboxylates, and the like; sulfonates such as alkylsulfonates, alkylbenzenesulfonates, alkylarylsulfonates, sulfonated fatty acid esters, and the like; sulfates such as sulfated alcohols, sulfated alcohol ethoxylates, sulfated alkylphenols, alkylsulfates, sulfosuccinates, alkylether sulfates, and the like; and phosphate esters such as alkylphosphate esters, and the like. Preferred anionics are sodium alkylarylsulfonate, alpha-olefinsulfonate, and fatty alcohol sulfates.

Cationic surfactants useful for inclusion in a cleaning composition include amines such as primary, secondary and tertiary monoamines with $C_{18}$ alkyl or alkenyl chains, ethoxylated alkylamines, alkoxylates of ethylenediamine, imidazoles such as a 1-(2-hydroxyethyl)-2-imidazoline, a 2-alkyl-1-(2-hydroxyethyl)-2-midazoline, and the like; and quaternary ammonium salts, as for example, alkylquaternary ammonium chloride surfactants such as n-alkyl($C_{12}$–$C_{18}$) dimethylbenzyl ammonium chloride, n-tetradecyldimethylbenzylammonium chloride monohydrate, a naphthylene-substituted quaternary ammonium chloride such as dimethyl-1-naphthylmethylammonium chloride, and the like; and other like cationic surfactants.

Surfactants can be used singly or in combination in the practice and utility of the present invention. In particular, nonionics and anionics can be used in combination. Semipolar nonionic, cationic, amphoteric and zwitterionic surfactants can be employed in combination with nonionics or anionics. The organic surfactant compounds can be formulated into any of the several commercially desirable composition forms of this invention having disclosed utility. Said compositions are washing or presoak treatments for soiled surfaces in concentrated form which, when dispensed or dissolved in water, properly diluted by a proportionating device, and delivered to the target surfaces as a solution, gel or foam will provide cleaning.

Metal Protecting Silicates

An effective amount of an alkaline metal silicate or hydrate thereof can be employed in the compositions and processes of the invention to form a stable solid cleaning composition that can have metal protecting capacity. The silicates employed in the compositions of the invention are known in the art. For example, typical alkali metal silicates are those powdered, particulate or granular silicates which are either anhydrous or preferably which contain water of hydration (5 to 25 wt-%, preferably 15 to 20 wt-% water of hydration). These silicates are preferably sodium silicates and have a $Na_2O:SiO_2$ ratio of about 1:1 to about 1:5, respectively, and typically contain available bound water in the amount of from 5 to about 25 wt-%. In general, the silicates employed in the present compositions have a $Na_2O:SiO_2$ ratio of 1:1 to about 1:3.75, preferably about 1:1.5 to about 1:3.75 and most preferably about 1:1.5 to about 1:2.5. A silicate with a $Na_2O:SiO_2$ ratio of about 1:2 and about 16 to 22 wt-% water of hydration, is most preferred. For example, such silicates are available in powder form as GD Silicate and in granular form as Britesil H-20, from PQ Corporation. These ratios may be obtained with single silicate compositions or combinations of silicates which upon combination result in the preferred ratio. The hydrated silicates at preferred ratios, a $Na_2O:SiO_2$ ratio of about 1:1.5 to about 1:2.5 have been found to provide the optimum metal protection and rapidly forming solid block detergent.

The amount of silicate used in forming the compositions of the invention tend to vary between 10 and 30 wt-%, preferably about 15 to 30 wt-% depending on degree of hydration. In one embodiment, the amount of silicate is in the range of 12–25 wt-%; preferably 15–30 wt-% of a hydrated silicate including 5 to 25% water. Generally, hydrated silicates are preferred.

Antimicrobial Agents

Antimicrobial agents are chemical compositions that can be used in a solid carbonate cleaning composition to prevent microbial contamination of instruments, such as medical and dental devices or instruments. Generally, these materials fall in specific classes including phenolics, halogen compounds, quaternary ammonium compounds, metal derivatives, amines, alkanol amines, nitro derivatives, analides, organosulfur and sulfur-nitrogen compounds and miscellaneous compounds. The given antimicrobial agent depending on chemical composition and concentration may simply limit further proliferation of numbers of the microbe or may destroy all or a substantial proportion of the microbial population. The terms "microbes" and "microorganisms" typically refer primarily to bacteria, fungi, viruses, and the like. In use, the antimicrobial agents are formed into a solid carbonate cleaning composition that when diluted and dispensed using an aqueous stream forms an aqueous disinfectant or sanitizer composition that can be contacted with a variety of surfaces resulting in prevention of growth or the killing of a substantial proportion of the microbial population. Common antimicrobial agents include phenolic antimicrobials such as pentachlorophenol, orthophenylphenol. Halogen containing antibacterial agents include sodium trichloroisocyanurate, iodine-poly(vinylpyrolidinonen) complexes, bromine compounds such as 2-bromo-2-nitropropane-1,3-diol quaternary antimicrobial agents such as benzalconium chloride, cetylpyridiniumchloride, amine and nitro containing antimicrobial compositions such as hexahydro-1,3,5-tris(2-hydroxyethyl)-s-triazine, dithiocarbamates such as sodium dimethyldithiocarbamate, and a variety of other materials known in the art for their microbial properties.

Defoaming Agents

A minor but effective amount of a defoaming agent for reducing the stability of foam may also be included in the present cleaning compositions. Preferably, the cleaning composition includes about 0.0001–5 wt-% of a defoaming agent, preferably about 0.01–3 wt-%.

Examples of defoaming agents suitable for use in the present compositions include silicone compounds such as silica dispersed in polydimethylsiloxane, fatty amides, hydrocarbon waxes, fatty acids, fatty esters, fatty alcohols, fatty acid soaps, ethoxylates, mineral oils, polyethylene glycol esters, alkyl phosphate esters such as monostearyl phosphate, and the like. A discussion of defoaming agents may be found, for example, in U.S. Pat. No. 3,048,548 to Martin et al., U.S. Pat. No. 3,334,147 to Brunelle et al., and U.S. Pat. No. 3,442,242 to Rue et al., the disclosures of which are incorporated by reference herein.

Dyes and Fragrances

Various dyes, odorants including perfumes, and other aesthetic enhancing agents may also be included in the composition. Dyes may be included to alter the appearance of the composition, as for example, Direct Blue 86 (Miles), Fastusol Blue (Mobay Chemical Corp.), Acid Orange 7 (American Cyanamid), Basic Violet 10 (Sandoz), Acid Yellow 23 (GAF), Acid Yellow 17 (Sigma Chemical), Sap Green (Keyston Analine and Chemical), Metanil Yellow (Keystone Analine and Chemical), Acid Blue 9 (Hilton Davis), Sandolan Blue/Acid Blue 182 (Sandoz), Hisol Fast Red (Capitol Color and Chemical), Fluorescein (Capitol Color and Chemical), Acid Green 25 (Ciba-Geigy), and the like.

Fragrances or perfumes that may be included in the compositions include, for example, terpenoids such as citronellol, aldehydes such as amyl cinnamaldehyde, a jasmine such as CIS-jasmine or jasmal, vanillin, and the like.

Anti-Redeposition Agents

A cleaning composition can also include an anti-redeposition agent, which can facilitate sustained suspension of soils in a cleaning solution and preventing the removed soils from being redeposited onto the substrate being cleaned. Examples of suitable anti-redeposition agents include fatty acid amides, fluorocarbon surfactants, complex phosphate esters, styrene maleic anhydride copolymers, and cellulosic derivatives such as hydroxyethyl cellulose, hydroxypropyl cellulose, and the like. A cleaning composition may include about 0.5–10 wt-%, preferably about 1–5 wt-%, of an anti-redeposition agent.

Rinse Aid Functional Materials

Functional materials of the invention can comprise a formulated rinse aid composition containing a wetting or sheeting agent combined with other optional ingredients in a solid block made using the hydrate complex of the invention. The rinse aid components of the cast solid rinse aid of the invention is a water soluble or dispersible low foaming organic material capable of reducing the surface tension of the rinse water to promote sheeting action and to prevent spotting or streaking caused by beaded water after rinsing is complete in warewashing processes. Such sheeting agents are typically organic surfactant like materials having a characteristic cloud point.

The cloud point of the surfactant rinse or sheeting agent is defined as the temperature at which a 1 wt. % aqueous solution of the surfactant turns cloudy when warmed. Since there are two general types of rinse cycles in commercial warewashing machines, a first type generally considered a sanitizing rinse cycle uses rinse water at a temperature of about 180° F., about 80° C. or higher. A second type of non-sanitizing machines uses a lower temperature non-sanitizing rinse, typically at a temperature of about 125° F., about 50° C. or higher. Surfactants useful in these applications are aqueous rinses having a cloud point greater than the available hot service water. Accordingly, the lowest useful cloud point measured for the surfactants of the invention is approximately 40° C. The cloud point can also be 60° C. or higher, 70° C. or higher, 80° C. or higher, etc., depending on the use locus hot water temperature and the temperature and type of rinse cycle.

Preferred sheeting agents, typically comprise a polyether compound prepared from ethylene oxide, propylene oxide, or a mixture in a homopolymer or block or heteric copolymer structure. Such polyether compounds are known as polyalkylene oxide polymers, polyoxyalkylene polymers or polyalkylene glycol polymers. Such sheeting agents require a region of relative hydrophobicity and a region of relative hydrophilicity to provide surfactant properties to the molecule. Such sheeting agents have a molecular weight in the range of about 500 to 15,000. Certain types of (PO)(EO) polymeric rinse aids have been found to be useful containing at least one block of poly(PO) and at least one block of poly(EO) in the polymer molecule. Additional blocks of poly(EO), poly PO or random polymerized regions can be formed in the molecule.

Particularly useful polyoxypropylene polyoxyethylene block copolymers are those comprising a center block of polyoxypropylene units and blocks of polyoxyethylene units to each side of the center block. Such polymers have the formula shown below:

$$(EO)_n\text{---}(PO)_m\text{---}(EO)_n$$

wherein n is an integer of 20 to 60, each end is independently an integer of 10 to 130. Another useful block copolymer are block copolymers having a center block of polyoxyethylene units and blocks of polyoxypropylene to each side of the center block. Such copolymers have the formula:

$$(PO)_n\text{---}(EO)_m\text{---}(PO)_n$$

wherein m is an integer of 15 to 175 and each end are independently integers of about 10 to 30.

The solid functional materials of the invention can often use a hydrotrope to aid in maintaining the solubility of sheeting or wetting agents. Hydrotropes can be used to modify the aqueous solution creating increased solubility for the organic material. Preferred hydrotropes are low molecular weight aromatic sulfonate materials such as xylene sulfonates and dialkyldiphenyl oxide sulfonate materials.

Bleaching Agent

Bleaching agents for use in inventive formulations for lightening or whitening a substrate, include bleaching compounds capable of liberating an active halogen species, such as $Cl_2$, $Br_2$, $-OCl^-$ and/or $-OBr^-$, under conditions typically encountered during the cleansing process. Suitable bleaching agents for use in the present cleaning compositions include, for example, chlorine-containing compounds such as a chlorine, a hypochlorite, chloramine. Preferred halogen-releasing compounds include the alkali metal dichloroisocyanurates, chlorinated trisodium phosphate, the alkali metal hypochlorites, monochloramine and dichloramine, and the like. Encapsulated chlorine sources may also be used to enhance the stability of the chlorine source in the composition (see, for example, U.S. Pat. Nos. 4,618,914 and 4,830,773, the disclosure of which is incorporated by reference herein). A bleaching agent may also be a peroxygen or active oxygen source such as hydrogen peroxide, perborates, sodium carbonate peroxyhydrate, phosphate peroxyhydrates, potassium permonosulfate, and sodium perborate mono and tetrahydrate, with and without activators such as tetraacetylethylene diamine, and the like. A cleaning composition may include a minor but effective amount of a bleaching agent, preferably about 0.1–10 wt. %, preferably about 1–6 wt. %.

Enzyme

The cleaning composition of the present invention can include one or more enzymes, which can provide desirable activity for removal of protein-based, carbohydrate-based, or triglyceride-based stains from substrates; for cleaning, destaining, and sanitizing, such as for medical and dental carts, cages, or instruments. Suitable enzymes include a protease, an amylase, a lipase, a gluconase, a cellulase, a peroxidase, or a mixture thereof of any suitable origin, such as vegetable, animal, bacterial, fungal or yeast origin. Preferred selections are influenced by factors such as pH-activity and/or stability optima, the most ability, and stability to active detergents, builders and the like. In this respect bacterial or fungal enzymes are preferred, such as bacterial amylases and proteases, and fungal cellulases. Preferably the enzyme is a protease, a lipase, an amylase, or a combination thereof. A suitable cleaning effect can be achieved with amounts of enzyme as low as about 0.1 wt-% of the solid carbonate cleaning composition. In the cleaning compositions of the present invention, suitable cleaning can typically be achieved when an enzyme is present at about 1 to about 30 wt-%; preferably about 2 to about 15 wt-%; preferably about 3 to about 10 wt-%; preferably about 4 to about 8 wt-%; preferably about 4, about 5, about 6, about 7, or about 8 wt-%. The higher enzyme levels are typically desirable in highly concentrated cleaning formulations.

Solid Rinse Compositions

Neutral Solid Rinse Compositions

A major component of the neutral solid rinse compositions employed in the present methods is the surfactant or surfactant system. The surfactants useful in these compositions are generally polyether (also known as polyalkylene oxide, polyoxyalkylene or polyalkylene glycol) compounds. More particularly, the polyether compounds are generally polyoxypropylene or polyoxyethylene glycol compounds. Typically, the useful surfactants are synthetic organic polyoxypropylene-polyoxyethylene block copolymers. The surfactant molecules typically have a particular stereochemistry which facilitates occlusion by or with urea. As a general rule, the useful surfactants will have a molecular weight in the range of about 700 to 14,000.

Certain types of polyoxypropylene-polyoxyethylene block copolymer surfactants have been found to be particularly useful. Those surfactants including a center block of polyoxypropylene units (PO), and having a block of polyoxyethylene (EO) units to each side of the center PO block, are generally useful in the present methods, particularly where the average molecular weight ranges from about 900 to 14,000, and the percent of weight EO ranges from about 10 to 80. These types of surfactants are sold commercially as "Pluronics" by the BASF Wyandotte Corporation, and are available under other trademarks from other chemical suppliers.

Also useful in the present methods are surfactants having a center block of polyoxyethylene units, with endblocks of polyoxypropylene units. These types of surfactants are known as "Reverse Pluronics", also available from Wyandotte.

Alcohol ethoxylates having EO and PO blocks can also be useful in the present methods. Straight chain primarily aliphatic alcohol ethoxylates can be particularly useful since the stereo chemistry of these compounds can permit occlusion by urea, and they can provide effective sheeting action. Such ethoxylates are available from several sources, including BASF Wyandotte where they are known as "Plurafac" surfactants. A particular group of alcohol ethoxylates found to be useful are those having the general formula R—(EO)$_m$(PO)$_n$, where m is an integer around 5, e.g. 2–7, and n is an integer around 13, e.g. 10–16. R can be any suitable radical, such as a straight chain alkyl group having from about 8 to 18 carbon atoms.

Another compound found to be useful is a surfactant having the formula

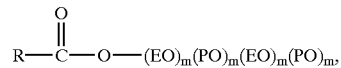

wherein m is an integer from about 18–22, preferably 20, and the surfactant has a molecular weight of from about 2,000 to 3,000, preferably about 2,500, a percent EO of about 36 to 44, preferably about 40, and where R is a straight chain alkyl group having from about 8 to 18 carbon atoms.

Certain surfactants have been found to be particularly preferred for use in this method, in view of the ease with which they combine with urea to form the solid neutral rinse compositions, and for the exceptionally effective sheeting action they provide in rinse compositions. One of the preferred surfactants is a block copolymer of the structure

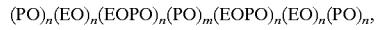

where m is an integer from 1–3 and each occurrence of n, independently, is an integer from 17–27, and EOPO represents a random mixture of EO and PO units at a ratio of EO to PO of from about 6:100 to 9:100. Preferably, the copolymer will be of the structure

where EOPO represents a random mixture of EO and PO units at a ratio of EO to PO of about 7:93. The preferred compound has an average molecular weight of between about 3,500–5,500, preferably about 4,500, and a weight percent of EO of about 25–35%, preferably about 30%.

A preferred combination includes the above-described copolymer having blocks of randomly mixed EO and PO units, and a surfactant having the formula (PO)(EO)(PO)(EO)(PO), with molecular weight of around 1,800–2,200 and a percent EO of about 25–30%. Preferably, the ratio of one copolymer to the other will range from about 2:1 to 0.5:1. Most preferably, the combination will include around 50% of each of the two copolymers.

Another preferred surfactant system includes from about 20 to 80% of the copolymer having blocks of randomly mixed EO and PO units previously described, from about 1–5% of a nonylphenolethoxylate, and from about 20 to 80% of a surfactant having the formula

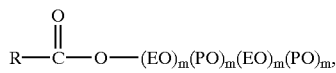

wherein m is an integer from about 18–22, preferably 20, and the surfactant has a molecular weight of from about 2,000 to 3,000, preferably about 2,500, a percent EO of about 36 to 44, preferably about 40, and where R is a straight chain alkyl group having from about 8 to 18 carbon atoms. More preferably, the components will be present in amounts of from 45 to 50%, 2 to 4%, and 45 to 50%, respectively.

The surfactant or surfactant system will form up to about 95% by weight of the total solid neutral rinse composition. Typically, the weight-percent surfactant will be in the range of about 60–90%, or more preferably, for improved rinse composition formation and sheeting action, in the range of about 80–90%.

Urea

Solid neutral rinse compositions employed in the present methods include a urea occlusion composition of an effective occlusion forming amount of urea and a compatible surfactant as previously described. It is believed that the urea reacts with the surfactant to form crystalline urea adducts or occlusion compounds, wherein the urea molecules are wrapped in a spiral or helical formation around the molecules of surfactant. Generally, urea will form occlusion compounds with long straight-chain molecules of 6 or more carbon atoms but not with branched or bulky molecules.

The solid neutral rinse compositions used in the present methods can include up to about 40% by weight urea. Typically, the compositions will have a minimum of about 5% urea. We have found that the preferred compositions, for reasons of economy, desired hardness and solubility, include about 8 to 40% urea. Most preferably, the compositions generally include about 10 to 15% urea.

Urea may be obtained from a variety of chemical suppliers, including Sohio Chemical Company, Nitrogen Chemicals Division. Typically, urea will be available in prilled form, and any industrial grade urea may be used in the context of this method.

Water

The solid neutral rinse composition employed in the present methods can also include water, which, it is believed, can aid in the occlusion reaction, by solubilizing the urea. The composition should include sufficient water to solubilize the urea. Typically, this requires a water:urea ratio greater than about 1:6. More preferably, for more effective formation and performance of the solid neutral rinse compositions, the water:urea ratio will be from about 1:3 to 1:5, and most preferably, about 1:4. Tap water, distilled water, deionized water or the like may be used. Water is the preferred solvent because of its nontoxicity and ready availability.

Dispensing Rate Adjusting Additive

Preferably, the solid neutral rinse compositions employed in the present methods include an effective dispensing rate modifying amount of a urea compatible additive, or dispensing rate adjusting additive. A dispensing rate adjusting additive is generally needed to provide for the desired rate of solubilization, when the solid neutral rinse composition is in use.

Many factors, or dispensing variables, affect the rate of solubilization or release of the surfactant from the solid neutral rinse composition. Four variables that can affect the dispensing rate are the temperature of the incoming water, pressure of the rinse water, the length of time of the cycle during which water contacts the solid neutral rinse composition to solubilize it, and the presence and design of a screen in the dispenser between the solid neutral rinse composition and the spray nozzle which directs water to the solid. While these variables can be adjusted to more nearly provide the desired dispensing rate, nevertheless we have found it desirable to include a dispensing rate adjusting additive within the composition itself. Use of the solid neutral rinse composition which includes a dispensing rate adjusting additive according to the present method generally provides acceptable dispensing through the dispenser under typical conditions found in institutional use. The variables such as temperature, pressure, time and a screen can then be adjusted if necessary to obtain more precisely the dispensing rate preferred in a particular situation.

We have found that without a dispensing rate adjusting additive, the solid neutral rinse compositions employed in the present methods can dispense more rapidly than necessary or desired. Preferably an effective dispensing rate modifying amount (generally up to about 5%) of a urea compatible dispensing rate adjusting additive is included in the solid neutral rinse compositions. Generally, any organic low molecular weight water insoluble additive which would not interfere with rinse performance may be utilized as the dispensing rate adjusting additive. Preferred additives include lauric acid, myristic acid, palmitic acid, stearic acid, oleic acid, alkanolamide compounds such as stearic or palmitic alkanolamide, silicone dimethyl polysiloxane compounds, and free acids of organic phosphate esters.

A preferred dispensing rate adjusting additive includes a phosphate ester of cetyl alcohol often available as a mixture of mono and di-cetyl phosphates. This additive is generally available as a nontoxic, nonhazardous solid or powder from well known chemical suppliers. This additive provides good dispensing rate modification and also has good defoaming properties.

For institutional solid neutral rinse compositions, the additive may be used in quantities up to about 5% by weight of the total solid composition. More preferably, it will be used in sufficient quantity to form about 0.3–1.0% by weight of the total composition. Expressed as parts per million, this dispensing provides a concentration of about 32 to 85 ppm solid neutral rinse composition in the rinse water. More preferably, the concentration will be between about 37 to 48, or around 41–43 ppm.

Other Components

The solid neutral rinse compositions employed in the present methods can also include components such as dyes, preservatives and the like, several of which are described herein above for the cleaning composition. While preservatives typically are not necessary in the context of this invention, they may be included where desired. Suitable preservatives include formaldehyde, glutaraldehyde, methyl-p-hydroxybenzoate, propyl-p-hydroxybenzoate, chloromethyl isophthiozolinone, methyl isophthiozolinone, and a $C_{12}$, $C_{11}$, $C_{16}$ dimethylbenzyl aluminum chloride such as that available as Hyamine 3500 from Rohm & Haas, and the like. Suitable preservatives may be obtained from a variety of well known chemical suppliers.

Solid Neutralizing Rinse Compositions

The methods of the invention can also employ a solid neutralizing rinse composition, such as a solid, low foaming, effective rinse composition formulated from components described in this section. One preferred requirement for a concentrated rinse composition is effective sheeting action and low foam in an aqueous rinse. Such concentrate materials can contain a nonionic block copolymer and a defoamer composition to provide basic rinse requirements. Such materials can contain an ethylene oxide-propylene oxide non-ionic block copolymer with a high cloud point. The nonionic block copolymer can commonly include compounds produced by polymerizing ethylene oxide and propylene oxide.

Illustrative but non-limiting examples of various suitable high cloud point nonionic surface active agents for these rinse compositions include polyoxyethylene-polyoxypropylene block copolymers having the formula:

$$(EO)_x(PO)_y(EO)_x$$

wherein x, y and z reflect the average molecular proportion of each alkylene oxide monomer in the overall block copolymer composition. x typically ranges from about 30 to 130, y typically ranges from about 30 to 70, z typically ranges from about 30 to 130, and x plus y is typically greater than about 60. The total polyoxyethylene component of the block copolymer constitutes typically at least about 40 mol-% of the block copolymer and commonly 75 mol-% or more of the block copolymer. The material preferably has a molecular weight greater than about 5,000 and more preferably greater than about 10,000.

An important characteristic of the nonionic block copolymers used in these rinse compositions is the cloud point of the material. The cloud point of nonionic surfactant of this class is defined as the temperature at which a 1 wt-% aqueous solution of the surfactant turns cloudy when it is heated.

Rinse cycles in medical cart washers typically employ rinse water at a temperature of at least about 40° C., preferably at least about 80° C. Rinse cycles in medical cage washers typically employ rinse water at a temperature of at least about 40° C., preferably at least about 80° C. Rinse cycles in medical instrument washers typically employ rinse water at a temperature of at least about 40° C., preferably at least about 80° C. A surfactant useful in any of these methods is an aqueous rinse having a cloud point greater than the available hot service water. Accordingly, the lowest useful cloud point, measured using a 1 wt-% aqueous solution, for the nonionics of the invention point is at least about 40° C., preferably at least about 50° C., preferably at least about 60° C., preferably at least about 70° C., preferably at least about 80° C., preferably at least about 90 to 100° C.

For the purpose of this invention, the term "rinse composition" includes solid materials that are dissolved or suspended in an aqueous stream or volume to produce an aqueous rinse. Accordingly, an aqueous rinse composition is an aqueous material that is contacted with a medical cart, cage, instrument, or other equipment in a rinse cycle. A sheeting agent is the polymeric material used to promote the even drainage of the aqueous rinse. Sheeting is defined as forming a continuous, evenly draining film, leaving virtually no spots or film upon the evaporation of water.

Defoaming agents (defoamers) include a variety of different materials adapted for defoaming a variety of compositions. Defoamers can include an anionic or nonionic material such as polyethylene glycol, polypropylene glycol, fatty acids and fatty acid derivatives, fatty acid sulfates, phosphate esters, sulfonated materials, silicone based compositions, and others.

Preferred defoamers include silicones and other types of active anti-foam agents. Silicone foam suppressors include polydialkylsiloxane preferably polydimethylsiloxane. Such silicone based foam suppressors can be combined with silica. Such silica materials can include silica, fumed silica, derivatized silica, silanated silica, etc. Commonly available anti-foaming agents combines a polydimethylsiloxane and silica gel.

Preferred defoamers include fatty acid defoamers. Such defoamer compositions can include simple alkali metal or alkaline earth metal salts of a fatty acid or fatty acid derivatives. Examples of such derivatives include mono, di- and tri-fatty acid esters of polyhydroxy compounds such as ethylene glycol, glycerine, propylene glycol, hexylene glycol, etc. Preferably such defoaming agents include a fatty acid monoester of glycerol. Fatty acids useful in such defoaming compositions can include any C8–24 saturated or unsaturated, branched or unbranched mono or polymeric fatty acid and salts thereof, including for example myristic acid, palmitic acid, stearic acid, behenic acid, lignoceric acid, palmitoleic acid, oleic acid, linoleic acid, arachidonic acid, and others commonly available.

Other suitable anti-foam agents include water insoluble waxes, preferably microcrystalline wax, petroleum wax, synthetic petroleum wax, rice base wax, beeswax having a melting point in the range from about 35° C. to 125° C. with a low saponification value, white oils, etc. Such materials are used in the rinse compositions of the invention at a sufficient concentration to prevent the accumulation of any measurable stable foam during a rinse cycle.

The solid rinse composition employed in the present methods can contain one or more solid water soluble fillers for the purpose of facilitating processing, product stability, or dispensing of the composition or contributing to other performance characteristics. Many different types of fillers may be utilized in the rinse composition, including specifically but not limited to such compounds as a sugar such glucose, fructose, sucrose; an alkali metal salt such as sodium chloride, potassium chloride, sodium carbonates, sodium bicarbonate, sodium sulfate, potassium sulfate, sodium acetate, sodium lactate, water soluble amino acids such as alanine, arginine, glycine, lysine, proline; phosphates such as tetrasodium pyrophosphate, sodium phosphate and others.

The solid neutralizing rinse composition employed in the present methods can contain a complexing or chelating agent that aids in reducing the harmful effects of hardness components in service water. Typically calcium, magnesium, iron, manganese, and other polyvalent metal cations, present in service water, can interfere with the action of either washing compositions or rinsing compositions. A chelating agent can effectively complex with and prevent such ions from the service water interfering with the action of an active component increasing rinse composition performance. Both organic and inorganic chelating agents are common. Inorganic chelating agents include such compounds as sodium pyrophosphate, and sodium tripolyphosphate. Organic chelating agents include both polymeric and small molecule chelating agents. Polymeric chelating agents commonly include ionomer compositions such as polyacrylic acids compounds. Small molecule organic chelating agents include salts of ethylenediaminetetracetic acid (EDTA) and hydroxyethylenediaminetetracetic acid, nitrilotriacetic acid, ethylenediaminetetrapropionates, triethylenetetraminehexacetates, and the respective alkali metal ammonium and substituted ammonium salts thereof. Amino-phosphates are also suitable for use as chelating agents in the composition of the invention and include ethylenediamine tetra(methylenephosphonates), nitrilotrismethylenephosphonates, diethylenetriaminepenta (methylene phosphonates). These amino phosphonates commonly contain alkyl or alkylene groups with less than 8 carbon atoms. Preferred chelating agents include the disodium salt of ethylenediaminetetracetic acid.

Certain organic components of the solid rinse composition employed in the present methods can be subject to microbial or chemical decomposition. Organic materials are commonly useful in stabilizing the mixtures. Preferred preservatives or stabilizers for the invention include C1–10 mono, di- and tricarboxylic acid compounds. Preferred examples of such acids include acetic acid, citric acid, benzoic, sorbic, lactic, maleic, tartaric and fumaric.

Optional ingredients which can be included in the solid rinse composition in conventional levels for use include solvents, hydrotropes, processing aids, corrosion inhibitors, dyes, fillers, optical brighteners, germicides, pH adjusting agents (monoethanolamine, sodium carbonate, sodium hydroxide, hydrochloric acid, phosphoric acid, et cetera), bleaches, bleach activators, perfumes, and the like.

Solid neutralizing rinse compositions can be formed by incorporating into the composition a casting agent. Typically organic and inorganic solidifying materials can be used to render the composition solid. Preferably organic materials are used because inorganic compositions tend to promote spotting in a rinse cycle. Preferred casting agents include polyethylene glycol and an inclusion complex comprising urea and a nonionic polyethylene or polypropylene oxide polymer. Polyethylene glycols (PEG) are used in melt type solidification processing by uniformly blending the sheeting agent and other components with PEG at a temperature above the melting point of the PEG and cooling the uniform mixture. An inclusion complex solidifying scheme is set forth in Morganson et al., U.S. Pat. No. 4,647,258. Preferred casting agents include carbonate based binders, such as those described hereinabove for the cleaning composition.

Certain Preferred components of the solid rinse compositions employed in the present methods are set forth in the table below.

| Solid Rinse Composition Proportions (wt.-%) | | | |
|---|---|---|---|
| | Useful | Preferred | Preferred |
| Nonionic Sheeting Agent | 0.1–50 | 5–40 | 10–30 |
| Defoamer | 0.1–30 | 0.2–25 | 1–15 |
| Thickener | 0–5 | 0–4 | 0.1–1 |
| Preservative | 0.001–1 | 0.01–0.5 | 0.025–0.2 |
| Solidifying System | 0–25 | 0.01–15 | 0.5–0 |
| Diluent | Balance | Balance | Balance |

Cast solid products can be conveniently dispensed by inserting a cast solid material in a container or with no enclosure into a spray-type dispenser such as the volume SOL-ET controlled ECOTEMP Rinse Injection Cylinder system manufactured by Ecolab Inc., St. Paul, Minn. Such a dispenser cooperates with a warewashing machine in the rinse cycle. When demanded by the machine, the dispenser directs a spray of water onto the cast solid block of rinse composition which effectively dissolves a portion of the block creating a concentrated aqueous rinse solution which is then fed directly into the rinse water forming the aqueous rinse. The aqueous rinse is then contacted with the dishes to affect a complete rinse. This dispenser and other similar dispensers are capable of controlling the effective concentration of the active block copolymer in the aqueous rinse by measuring the volume of material dispensed, the actual concentration of the material in the rinse water (an electrolyte measured with an electrode) or by measuring the time of the spray on the cast block.

Solid Antimicrobial Compositions

The methods of the present invention can employ any of a variety of solid antimicrobial compositions. For use in the present methods, the solid antimicrobial composition must suspend or dissolve in a carrier, such as water, at a concentration high enough to exhibit effective antimicrobial, sanitizing, or disinfecting action. Suitable solid antimicrobial compositions can include antimicrobial agents such as quaternary ammonium antimicrobial agents, acid sanitizers, and other health care surface compatible antimicrobial agents. Certain of these antimicrobial agents are solid at ambient temperatures and can be used as is or formulated with an appropriate filler. These antimicrobial agents can be formulated as solids by methods known to those of skill in the art.

Quaternary Ammonium Antimicrobial Agents

Quaternary ammonium antimicrobial agents are useful in the present methods, due to their commercial availability, easy incorporation into solid formulas and high sanitizing efficacy. These antimicrobial agents are also preferred because of their compatibility to high water temperatures to the presence of high organic loads, stability and broad spectrum antimicrobial efficacy in variable high and low pH wash systems, inherent chemical deodorizing, and their non-staining, non-bleaching, non-corrosive nature.

Suitable agents which may be incorporated are quaternary ammonium salts of the formula:

in which at least one, but not more than two, of $R_1$, $R_2$, $R_3$, and $R_4$ is an organic radical containing a group selected from a $C_{16}$–$C_{22}$ aliphatic radical, or an alkyl phenyl or alkyl benzyl radical having 10–16 atoms in the alkyl chain, the remaining group or groups being selected from hydrocarbyl groups containing from 1 to about 4 carbon atoms, or $C_2$–$C_4$ hydroxy alkyl groups and cyclic structures in which the nitrogen atom forms part of the ring, and Y is an anion such as halide, methylsulphate, or ethylsulphate.

In the context of the above definition, the hydrophobic moiety (i.e. the $C_{16}$–$C_{22}$ aliphatic, $C_{10}$–$C_{16}$ alkyl phenyl or alkyl benzyl radical) in the organic radical may be directly attached to the quaternary nitrogen atom or may be indirectly attached thereto through an amide, esters, alkoxy, ether, or like grouping.

Illustrative quaternary ammonium salts include distearyl dimethyl ammonium chloride, stearyl dimethyl benzyl ammonium chloride, coconut alkyl dimethyl benzyl ammonium chloride, dicoconut alkyl dimethyl ammonium bromide, cetyl pyridinium iodide, cetyl pyridinium iodide, cetyl trimethyl ammonium bromide, octyl decyl dimethyl ammonium chloride, dioctyl dimethyl ammonium chloride, didecyl dimethyl ammonium chloride, dimethyl benzyl ammonium chloride, and the like. Preferred quaternary ammonium salts include octyl decyl dimethyl ammonium chloride, dioctyl dimethyl ammonium chloride, didecyl dimethyl ammonium chloride, dimethyl benzyl ammonium chloride, or combinations thereof, and the like. A preferred mixture of quaternary ammonium salts includes octyl decyl dimethyl ammonium chloride, dioctyl dimethyl ammonium chloride, didecyl dimethyl ammonium chloride, and dimethyl benzyl ammonium chloride.

Fatty Acid Sanitizers

Suitable fatty acids for the solid antimicrobial composition include an aliphatic or aromatic fatty acid, either saturated or unsaturated, preferably, saturated, and having from about 6 to about 20 carbon atoms and, preferably, from about 8 to about 12 carbon atoms, as well as mixtures thereof. The fatty acid may be linear, branched or cyclic and may contain substituent atoms such as hydroxyl groups or ether linkages as long as the substituents do not affect antimicrobial activity. Representative of the fatty acids contemplated for use herein include caproic acid, caprylic acid, capric acid, lauric acid, and octanoic acid as well as mixtures thereof.

Other Health Care Surface Compatible Antimicrobial Agents

Other health care surface compatible antimicrobial agents include aldehyde antimicrobial agents; carboxylic acid antimicrobial agents; peracid and peroxygen antimicrobial agents; ozone; organic halogen, inorganic halogen, neutral oxide of a halogen (e.g. chlorine dioxide), and halogen releasing antimicrobial agents, such as iodine, iodine complexes, interhalogens, chlorine sodium trichloroisocyanurate, iodine-poly(vinylpyrolidinonen) complexes, 2-bromo-2-nitropropane-1,3-diol, chlorinated phosphates, such as chlorinated trisodium phosphate; phenolic antimicrobial agents (e.g., pentachlorophenol and orthophenylphenol); surface-active antimicrobial agents, such as acid-anionic, amphoteric and cationic surfactants; nitrogen containing antimicrobial agents and polymers, such as alkylamines alkanol amines, nitro derivatives, and analides; metal derivatives; organosulfur and sulfur-nitrogen compounds; and the like; and mixtures thereof. These various antimicrobial agents are known to those of skill in the art and can be employed in the methods of the present invention. Preferred antimicrobial agents include chlorinated phosphates, such as chlorinated trisodium phosphate.

Other Ingredients

Chelating agents can be added with any of these antimicrobial agents to the composition to enhance biological activity and cleaning performance. For example, one-hydroxy ethylidene-1, one-di-phosphonic acid commercially available from the Monsanto Company under the trade designation "Dequest" has been found to assist in the disruption of cell structure of the polysaccharide-divalent metal ion complex thought to exist in gram negative microorganisms. Citric acid is also found to interrupt such gram negative microorganism complexes. Other materials which are sufficiently stable at low pH may be added to the composition to impart desirable qualities depending upon the intended ultimate use.

Alkyl phosphate esters possess some antimicrobial activity in their own right under the conditions of the present invention. This antimicrobial activity also tends to add to the overall antimicrobial activity of the present compositions even though the phosphate esters may be added for other reasons.

Concentrate and Use Compositions

The present solid carbonate cleaning compositions can be dissolved in a carrier, typically water, to form concentrate and use compositions. The solid can be dissolved in water to form a concentrate composition, which can then be further diluted to a use composition. The solid can yield concentrate compositions that include up to about 2 to about 4 wt-% of the solid carbonate cleaning composition with the remainder typically being carrier. Concentrate compositions can have concentrations of solid carbonate cleaning composition as low as about 0.3 wt-%. The solid carbonate cleaning composition can also be dissolved at lower concentrations, for example as low as 0.03 wt-%, to form concentrate or use compositions. Use compositions can be obtained directly by dissolving the solid composition in about 500 parts of water or at a concentration of about 300 to about 8000 ppm. Preferred use compositions include about 0.03 to about 1 wt-% solid carbonate cleaning composition.

According to the manual cleaning method aspect of this invention, soiled medical or dental carts, cages, instruments, devices, or portions thereof are contacted with an effective amount, typically from about 0.03% to about 0.8% by weight, preferably from about 0.2% to about 0.4% by weight, of the composition of the present invention.

The present solid rinse compositions can be dissolved in a carrier, typically water, to form concentrate and use compositions. The solid can be dissolved in water to form a concentrate composition, which can then be further diluted to a use composition. The solid can yield concentrate compositions that include up to about 2 to about 4 wt-% of the solid rinse composition with the remainder typically being carrier. Concentrate compositions can have concentrations of solid rinse composition as low as about 0.3 wt-%. The solid rinse composition can also be dissolved at lower concentrations, for example as low as 0.03 wt-%, to form concentrate or use compositions. Use compositions can be obtained directly by dissolving the solid rinse composition in about 500 parts of water or at a concentration of about 300 to about 8000 ppm. Preferred use compositions include about 0.03 to about 1 wt-% solid rinse composition.

The present solid antimicrobial compositions can be dissolved in a carrier, typically water, to form concentrate and use compositions. The solid can be dissolved in water to form a concentrate composition, which can then be further diluted to a use composition. The solid can yield concentrate compositions that include amounts of the antimicrobial composition that yield effective antimicrobial activity, effective sanitizing activity, and/or effective disinfecting activity. For example, the concentrate can include up to about 0.6 to about 10 wt-% of the solid antimicrobial composition with the remainder typically being carrier. Concentrate compositions can have concentrations of solid antimicrobial composition as low as about 0.2 wt-%. The solid antimicrobial composition can also be dissolved at lower concentrations, for example as low as about 0.01 to about 5 wt-%, to form use compositions. Preferred use compositions include about 0.1 to about 2 wt-% solid antimicrobial composition. A solid antimicrobial composition can include about 0.5 to about 20 wt-% antimicrobial agent.

Dispensing Use or Concentrate Compositions

The compositions employed in the present invention can be used in a variety of machines that wash, rinse, sanitize, and/or disinfect medical or dental carts, cages, instruments or devices. Such machines can be charged manually with powder or other solid forms of the composition. Such machines can also automatically dispense the present compositions. Such dispensing can include dissolving the solid composition to form a liquid concentrate composition, optionally diluting the first liquid concentrate composition to yield a second liquid concentrate composition (that is less concentrated), and diluting the liquid concentrate into a chamber to form the use composition.

The first liquid concentrate composition can take the form of a solution, suspension, or slurry. The first concentrate can be fed by gravity or pumped into the liquid to form the use composition. For example, the first concentrate composition can be formed by running water over the solid composition. The water can drain from the first vessel containing the solid composition through a port. The port can be opened and closed by a valve, such as a solenoid valve. The first vessel can drain into a second vessel, for example a vessel suitable for containing and dispensing a liquid cleaning, rinsing, or antimicrobial composition into an apparatus. The apparatus typically includes a pump or other transfer device for transporting the first concentrate composition from the second vessel into the apparatus where it is diluted to a use composition. The use composition can be used to immerse or spray the medical carts, cages, instruments, or devices.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

All publications and patent applications in this specification are indicative of the level of ordinary skill in the art to which this invention pertains.

The invention has been described with reference to various specific and preferred embodiments and techniques. However, it should be understood that many variations and modifications may be made while remaining within the spirit and scope of the invention.

We claim:

1. A method of cleaning a medical cart, cage, instrument, or device, comprising:
dissolving a solid carbonate cleaning composition in water,
the solid carbonate cleaning composition comprising:
about 10 to 80 wt-% of Na$_2$CO$_3$, and
an effective sequestering amount of an organic phosphonate hardness sequestering agent;
wherein the solid carbonate cleaning composition comprises:
non-hydrated sodium carbonate, and
a binding agent comprising hydrated sodium carbonate and organic phosphonate;
contacting the medical cart, cage, instrument, or device wit the dissolved carbonate cleaning composition at a temperature at or above ambient temperature;
dissolving a solid rinse composition in water; and
rinsing the medical cart, cage, instrument, or device with the dissolved rinse composition.

2. The method of claim 1, wherein the solid rinse composition comprises a nonionic surfactant and urea.

3. The method of claim 2, wherein the solid rinse composition comprises:
about 5 to about 40 wt-% urea
about 60 to about 90 wt-% of one or more EO-PO block copolymer surfactants; and
water to provide a water:urea weight ratio of about 1:3 to about 1:6.

4. The method of claim 1, wherein the solid rinse composition comprises:
about 1 to 25 wt-% of a nonionic block copolymer composition, having the formula:

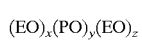

with a molecular weight between 10,000 and 15,000,
wherein x is 30 to 130,
y is 30 to 70,
z is 30 to 130, and
x+y is $\geq 60$,
having a cloud point, measured wit a 1 wt-% aqueous solution, of greater than 100° C.;

about 1 to 25 wt-% of a defoamer composition; and
about 3 to 80 wt-% of a water soluble casting agent.

5. The method of claim 1, further comprising:
dissolving a solid antimicrobial composition in water; and
contacting the medical cart, cage, instrument, or device with the dissolved antimicrobial composition at a temperature at or above ambient temperature.

6. The meted of claim 1, wherein the solid cleaning composition is substantially free of a second source of alkalinity.

7. The method of claim the solid cleaning composition further comprises alkali metal silicate having a M$_2$O:SiO$_2$ ratio of about 1:1 to 1:5.

8. The of claim 1, wherein the binding agent:
is dispersed throughout the solid cleaning composition;
comprises, for each mole of the organic sequestrant, about 3 to 10 moles of the carbonate monohydrate and 5 to 15 moles of water; and
has a melting transition temperature of greater than about 120° C.

9. The method of claim 1, comprising cleaning a medical instrument, the medical comprising a forceps, scissor, shear, saw, hemostat, knife, chisel, rongeur, file, nipper, drill, drill bit, rasp, burr, spreader, breaker, clamp, needle holder, carrier, clip, hook, gouge, curette, retractor, straightener, punch, extractor, scoop, keratoine, expresser, trocar, dilator, cage, catheter, cannula, plug, stent, arthoscope, or combinations thereof.

10. A method of cleaning a medical cart, cage, instrument, or device, comprising:
dissolving a solid carbonate cleaning composition in water,
the solid carbonate cleaning composition comprising:
about 10 to 80 wt-% of Na$_2$CO$_3$, and
an effective sequestering amount of an organic phosphonate hardness sequestering agent;
wherein the solid carbonate cleaning composition comprises:
non-hydrated sodium carbonate, and
a binding agent comprising hydrated sodium carbonate and organic phosphonate;
contacting the medical cart, cage, instrument or device with the dissolved carbonate cleaning composition at a temperature at or above ambient temperature;
dissolving a solid antimicrobial composition in water; and
contacting the medical cart, cage, instrument, or device with the dissolved antimicrobial composition at a temperature at or above ambient temperature.

11. The method of claim 10, wherein the solid antimicrobial composition comprises a solid quaternary ammonium antimicrobial agent or a solid halogen antimicrobial agent.

12. The method of claim 11, wherein the solid quaternary ammonium antimicrobial agent comprises octyl decyl dimethyl ammonium chloride, dioctyl dimethyl ammonium chloride, didecyl dimethyl ammonium chloride, and dimethyl benzyl ammonium chloride.

13. The method of claim 12, wherein the solid halogen antimicrobial agent comprises chlorinated trisodium phosphate.

14. The method of claim 10, wherein the contacting continues for a time and at a concentration of antimicrobial composition sufficient for sanitizing the medical cart, cage, instrument, or device.

15. The method of claim 10, wherein the contacting continues for a time and at a concentration of antimicrobial composition sufficient for disinfecting the medical cart, cage, instrument, or device.

16. The method of claim 15, wherein the solid antimicrobial composition comprises octyl decyl dimethyl ammonium chloride, dioctyl dimethyl ammonium chloride, didecyl dimethyl ammonium chloride, dimethyl benzyl ammonium chloride, or a combination thereof.

17. The method of claim 10, wherein the solid cleaning composition is substantially free of a second source of alkalinity.

18. The method of claim 10, wherein the solid cleaning composition further comprises an alkali metal silicate having a $M_2O:SiO_2$ ratio of about 1:1 to 1:5.

19. The method of claim 10, wherein the binding agent:
is dispersed throughout solid cleaning composition;
comprises, for each mole of the organic sequestrant, about 3 to 10 moles of the carbonate monohydrate and 5 to 15 moles of water; and
has a melting transition temperature of greater than about 120° C.

20. The method of claim 10, further comprising:
dissolving a solid rinse composition in water; and
rinsing the medical cart, cage, instrument, or device with the dissolved rinse composition.

21. The method of claim 10, comprising cleaning a medical instrument, the medical instrument comprising a forceps, scissor, shear, saw, hemostat, knife, chisel, rongeur, file, nipper, drill, drill bit, rasp, bun, spreader, breaker, clamp, needle holder, carrier, clip, hook, gouge, curette, retractor, straightener, punch, extractor, scoop, keratome, expressor, trocar, dilator, cage, catheter, cannula, plug, stent, arthoscope, or combinations thereof.

22. A method of cleaning a medical cart, cage, instrument, or device, comprising:
dissolving a solid carbonate cleaning composition in water,
the solid carbonate cleaning composition comprising:
about 10 to 80 wt-% of $Na_2CO_3$,
an effective sequestering amount of an organic phosphonate hardness sequestering agent, and
an alkali metal silicate having a $M_2O:SiO_2$ ratio of about 1:1 to 1:5;
wherein the solid cleaning composition comprises:
non-hydrated sodium carbonate, and
a binding agent comprising hydrated sodium carbonate and organic phosphonate; and
contacting the medical cart, cage, instrument, or device with the dissolved carbonate cleaning composition at a temperature at or above ambient temperature.

23. The method of claim 22, wherein the solid carbonate cleaning composition further comprises less than about 10 wt-% of alkali metal hydroxide.

24. The method of claim 23, wherein the solid cleaning composition is substantially free of a second source of alkalinity.

25. The method of claim 22, wherein the solid carbonate cleaning composition further comprises about 10 to about 30 wt-% of the alkali metal silicate.

26. The method of claim 22, wherein the binding agent:
is dispersed throughout the solid cleaning composition
comprises, for each mole of the organic sequestrant, about 3 to 10 moles of the carbonate monohydrate and 5 to 15 moles of water; and has a melting transition temperature of greater than about 120° C.

27. The method of claim 22, further comprising:
dissolving a solid rinse composition in water; and
rinsing the medical cart, cage, instrument, or device with the dissolved rinse composition.

28. The method of claim 27, wherein the solid rinse composition comprises a nonionic surfactant and urea.

29. The method of claim 28, wherein the solid rinse composition comprises:
about 5 to about 40 wt-% urea
about 60 to about 90 wt-% of one or more BO-PO block copolymer surfactants; and
water to provide a water:urea weight ratio of about 1:3 to about 1:6.

30. The method of claim 27, wherein the solid rinse composition comprises:
about 1 to 25 wt-% of a nonionic block copolymer composition, having the formula:

$$(EO)_x(PO)_y(EO)_z$$

with a molecular weight between 10,000 and 15,000,
wherein x is 30 to 130,
y is 30 to 70,
z is 30 to 130, and
x+y is $\geq 60$,
having a cloud point, measured with a 1 wt-% aqueous solution, of greater than 100° C.;
about 1 to 25 wt-% of a defoamer composition; and
about 3 to 80 wt-% of a water soluble casting agent.

31. The method of claim 27, further comprising:
dissolving a solid antimicrobial composition in water; and
contacting the medical cart, cage, instrument, or device with the dissolved antimicrobial composition at a temperature at or above ambient temperature.

32. The method of claim 22, further comprising:
dissolving a solid antimicrobial composition in water; and
contacting the medical cart, cage, instrument, or device with the dissolved antimicrobial composition at a temperature at or above ambient temperature.

33. The method of claim 32, wherein the solid antimicrobial composition comprises a solid quaternary ammonium antimicrobial agent or a solid halogen antimicrobial agent.

34. The method of claim 33, wherein the solid quaternary ammonium antimicrobial agent comprises octyl decyl dimethyl ammonium chloride, dioctyl dimethyl ammonium chloride, didecyl dimethyl ammonium chloride, and dimethyl benzyl ammonium chloride.

35. The method of claim 33, wherein the solid halogen antimicrobial agent comprises chlorinated trisodium phosphate.

36. The method of claim 32, wherein the contacting continues for a time and at a concentration of antimicrobial composition sufficient for sanitizing the medical cart, cage, instrument, or device.

37. The method of claim 32, wherein the contacting continues for a time and at a concentration of antimicrobial composition sufficient for disinfecting the medical cart, cage, instrument, or device.

38. The method of claim 37, wherein the solid antimicrobial composition comprises octyl decyl dimethyl ammonium chloride, dioctyl dimethyl ammonium chloride, didecyl dimethyl ammonium chloride, dimethyl benzyl ammonium chloride, or a combination thereof.

39. The method of claim 22, comprising cleaning a medical instrument, the medical instrument comprising a forceps, scissor, shear, saw, hemostat, knife, chisel, rongeur, file, nipper, drill, drill bit, rasp, burr, spreader, breaker, clamp, needle holder, carrier, clip, hook, gouge, curette, retractor, straightener, punch, extractor, scoop, keratome, expressor, trocar, dilator, cage, catheter, cannula, plug, stent, arthoscope, or combinations thereof.

40. A method of cleaning a medical cart, cage, instrument, or device, comprising;
dissolving a solid carbonate cleaning composition in water,
the solid carbonate cleaning composition comprising:
about 10 to 80 wt-% of $Na_2CO_3$, and
an effective sequestering amount of an organic phosphonate hardness sequestering agent,
wherein the solid cleaning composition comprises non-hydrated sodium carbonate, and
a binding agent comprising hydrated sodium carbonate and organic phosphonate;
wherein the binding agent:
is dispersed throughout the solid cleaning composition;
comprises, for each mole of the organic sequestrant, about 3 to 10 moles of the carbonate monohydrate and 5 to 15 moles of water; and
has a molting transition temperature of greater than about 120° C.; and
contacting the medical cart, cage, instrument, or device with the dissolved carbonate cleaning composition at a temperature at or above ambient temperature.

41. The method of claim 40, wherein the solid carbonate cleaning composition further comprises less than about 10 wt-% of alkali metal hydroxide.

42. The method of claim 41, wherein the solid cleaning composition is substantially free of a second source of alkalinity.

43. The method of claim 40, wherein the solid cleaning composition further comprises an alkali metal silicate having a $M_2O:SiO_2$ ratio of about 1:1 to 1:5.

44. The method of claim 43, wherein the solid carbonate cleaning composition comprises about 10 to about 30 wt-% of the alkali metal silicate.

45. The method of claim 40, further comprising:
dissolving a solid rinse composition in water; and
rinsing the medical cart, cage, instrument, or device with the dissolved rinse composition.

46. The method of claim 45, wherein the solid rinse composition comprises a nonionic surfactant and urea.

47. The method of claim 46, wherein the solid rinse composition comprises:
about 5 to about 40 wt-% urea
about 60 to about 90 wt-% of one or more EO-PO block copolymer surfactants; and
water to provide a water:urea weight ratio of about 1:3 to about 1:6.

48. The method of claim 45, wherein the solid rinse composition comprises:
about 1 to 25 wt-% of a nonionic block copolymer composition, having the formula:

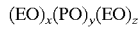

with a molecular weight between 10,000 and 15,000,
wherein x is 30 to 130,
y is 30 to 70,
z is 30 to 130, and
x+y is ≧60,
having a cloud point, measured with a 1 wt-% aqueous solution, of greater than 100° C.;

about 1 to 25 wt-% of a defoamer composition; and
about 3 to 80 wt-% of a water soluble casting agent.

49. The method of claim 45, further comprising:
dissolving a solid antimicrobial composition in water; and
contacting the medical cart, cage, instrument, or device with the dissolved antimicrobial composition at a temperature at or above ambient temperature.

50. The method of claim 40, further comprising:
dissolving a solid antimicrobial composition in water; and
contacting the medical cart, cage, instrument, or device with the dissolved antimicrobial composition at a temperature at or above ambient temperature.

51. The method of claim 50, wherein the solid antimicrobial composition comprises antimicrobial agent or a solid halogen antimicrobial agent.

52. The method of claim 51, wherein the solid quaternary ammonium antimicrobial agent comprises octyl decyl dimethyl ammonium chloride, dioctyl dimethyl ammonium didecyl dimethyl ammonium chloride, and dimethyl benzyl ammonium chloride.

53. The method of claim 51, wherein the solid halogen antimicrobial agent comprises chlorinated trisodium phosphate.

54. The method of claim 50, wherein the contacting continues for a time and at a concentration of antimicrobial composition sufficient for sanitizing the medical cart, cage, instrument, or device.

55. The method of claim 50, wherein the contacting continues for a time and at a concentration of antimicrobial composition sufficient for disinfecting the medical cart, cage, instrument, or device.

56. The method of claim 55, wherein the solid antimicrobial composition comprises octyl decyl dimethyl ammonium chloride, dioctyl dimethyl ammonium chloride, didecyl dimethyl ammonium chloride, dimethyl benzyl ammonium chloride, or a combination thereof.

57. The method of claim 40, comprising cleaning a medical instrument, the medical instrument comprising a forceps, scissor, shear, saw, hemostat, knife, chisel, rongeur, file, nipper, drill, drill bit, rasp, burr, spreader, breaker, clamp, needle holder, carrier, clip, hook, gouge, curette, retractor, straightener, punch, extractor, scoop, keratome, expressor, trocar, dilator, cage, catheter, cannula, plug, stein, arthoscope, or combinations thereof.

58. A method of cleaning a medical cart, cage, instrument, or device, comprising:
dissolving a solid carbonate cleaning composition in water,
the solid carbonate cleaning composition comprising:
about 20 to about 55 wt-% of $Na_2CO_3$,
about 3 to about 15 wt-% of an organic phosphonate hardness sequestering agent, and
about 0.1 to about 20 wt-% surfactant;
wherein the solid cleaning composition comprises: non-hydrated sodium carbonate, and
a binding agent comprising hydrated sodium carbonate and organic phosphonate; and
contacting the medical cart, cage, instrument, or device with the dissolved carbonate cleaning composition at a temperature at or above ambient temperature.

59. The method of claim 58, wherein the solid carbonate cleaning composition further comprises about 10 to about 30 wt-% of an alkali metal silicate having a $M_2O:SiO_2$ ratio of about 1:1 to 1:5.

60. The method of claim 58, wherein the solid carbonate cleaning composition further comprises less than about 10 wt-% of alkali metal hydroxide.

61. The method of claim 58, wherein the solid carbonate cleaning composition further comprises less than about 10 wt-% of alkali metal hydroxide.

62. The method of claim 61, wherein the solid cleaning composition is substantially free of a second source of alkalinity.

63. The method of claim 58, wherein the solid cleaning composition further comprises an alkali metal silicate having a $M_2O:SiO_2$ ratio of about 1:1 to 1:5.

64. The method of claim 63, wherein the solid carbonate cleaning composition comprises about 10 to about 30 wt-% of the alkali metal silicate.

65. The method of claim 58, wherein the binding agent:
is dispersed throughout the solid cleaning composition;
comprises, for each mole of the organic sequestrant, about 3 to 10 moles of the carbonate monohydrate and 5 to 15 moles of water; and
has a melting transition temperature of greater than about 120° C.

66. The method of claim 58, further comprising:
dissolving a solid rinse composition in water; and
rinsing the medical cart, cage, instrument, or device with the dissolved rinse composition.

67. The method of claim 66, wherein the solid rinse composition comprises a nonionic surfactant and urea.

68. The method of claim 67, wherein the solid rinse composition comprises:
about 5 to about 40 wt-% urea
about 60 to about 90 wt-% of one or more EO-PC block copolymer surfactants; and
water to provide a water:urea weight ratio of about 1:3 to about 1:6.

69. The method of claim 66, wherein the solid rinse composition comprises:
about 1 to 25 wt-% of a nonionic block copolymer composition, having the formula:

with a molecular weight between 10,000 and 15,000,
wherein x is 30 to 130,
y is 30 to 70,
z is 30 to 130, and
x+y is $\geq 60$,
having a cloud point, measured with a 1 wt-% aqueous solution, of greater than 100° C.;
about 1 to 25 wt-% of a defoamer composition; and
about 3 to 80 wt-% of a water soluble casting agent.

70. The method of claim 66, further comprising:
dissolving a solid antimicrobial composition in water; and
contacting the medical cart, cage, instrument, or device wit the dissolved antimicrobial composition at a temperature at or above ambient temperature.

71. The method of claim 58, further comprising:
dissolving a solid antimicrobial composition in water; and
contacting the medical cart, cage, instrument, or device with the dissolved antimicrobial composition at a temperature at or above ambient temperature.

72. The method of claim 71, wherein the solid antimicrobial composition comprises a solid quaternary ammonium antimicrobial agent or a solid halogen antimicrobial agent.

73. The method of claim 72, the solid quaternary ammonium antimicrobial agent comprises octyl decyl dimethyl ammonium chloride, dioctyl dimethyl ammonium chloride, didecyl dimethyl ammonium chloride, and dimethyl benzyl ammonium chloride.

74. The method of claim 72, wherein the solid halogen antimicrobial agent comprises chlorinated trisodium phosphate.

75. The method of claim 71, wherein the contacting continues for a time and at a concentration of antimicrobial composition sufficient for sanitizing the medical cart, cage, instrument, or device.

76. The method of claim 71, wherein the contacting continues for a time and at a concentration of antimicrobial composition sufficient for disinfecting the medical cart, cage, instrument, or device.

77. The method of claim 76, wherein the solid antimicrobial composition comprises octyl decyl dimethyl ammonium chloride, dioctyl dimethyl ammonium chloride, didecyl dimethyl ammonium chloride, dimethyl benzyl ammonium chloride, or a combination thereof.

78. The method of claim 58, comprising cleaning a medical instrument, the medical instrument comprising a forceps, scissor, shear, saw, hemostat, knife, chisel, rongeur, file, nipper, drill, drill bit, rasp, burr, spreader, breaker, clamp, needle holder, carrier, clip, hook, gouge, curette, retractor, straightener, punch, extractor, scoop, keratome, expressor, trocar, dilator, cage, catheter, cannula, plug, stent, arthoscope, or combinations thereof.

* * * * *